United States Patent
Fukuoka et al.

(10) Patent No.: US 10,518,025 B2
(45) Date of Patent: Dec. 31, 2019

(54) INFUSION SET

(71) Applicant: KOBAYASHI & CO., LTD., Tokyo (JP)

(72) Inventors: Koji Fukuoka, Kobe (JP); Go Kawaoi, Kobe (JP); Kazuyuki Osawa, Kobe (JP); Imari Endo, Kobe (JP)

(73) Assignee: KOBAYASHI & CO., LTD., Tokyo (JP)

( * ) Notice: Subject to any disclaimer, the term of this patent is extended or adjusted under 35 U.S.C. 154(b) by 324 days.

(21) Appl. No.: 15/549,542

(22) PCT Filed: Feb. 9, 2015

(86) PCT No.: PCT/JP2015/053565
§ 371 (c)(1),
(2) Date: Aug. 8, 2017

(87) PCT Pub. No.: WO2016/129046
PCT Pub. Date: Aug. 18, 2016

(65) Prior Publication Data
US 2018/0021512 A1    Jan. 25, 2018

(51) Int. Cl.
*A61M 5/14* (2006.01)
*A61J 1/10* (2006.01)
(Continued)

(52) U.S. Cl.
CPC ............... *A61M 5/14* (2013.01); *A61J 1/10* (2013.01); *A61M 5/1411* (2013.01);
(Continued)

(58) Field of Classification Search
CPC .... A61M 5/1626; A61M 5/14; A61M 5/1408; A61M 5/1411; A61M 5/1413;
(Continued)

(56) References Cited

U.S. PATENT DOCUMENTS

| | | |
|---|---|---|
| 2004/0097896 A1 | 5/2004 | Raufman et al. |
| 2011/0132482 A1* | 6/2011 | Honma ............... A61M 5/36 137/605 |
| 2015/0297830 A1 | 10/2015 | Okiyama |

FOREIGN PATENT DOCUMENTS

| | | |
|---|---|---|
| JP | 8-336601 A | 12/1996 |
| JP | 10-108908 A | 4/1998 |

(Continued)

OTHER PUBLICATIONS

International Search Report dated May 19, 2015, issued in counterpart International Application No. PCT/JP2015/053565 (2 pages).

*Primary Examiner* — Philip R Wiest
(74) *Attorney, Agent, or Firm* — Westerman, Hattori, Daniels & Adrian, LLP

(57) ABSTRACT

In an infusion set, a spike or a connector for connection with an intravenous drip needle is covered by a cap, arranged at which there is an opening configured so as to not allow passage therethrough of solid or liquid but so as to allow passage therethrough of gas at the interior of the cap, a hydrophobic filter being arranged at a location inward from where the tip of the spike or the connector for connection with an intravenous drip needle is inserted at the interior of the cap by way of an insertion port, and a lid at the exterior of said opening for closing said opening. A three-way stopcock having a primary tubing downstream branch connector equipped with a mechanism that connects in such fashion as to permit rotation about primary tubing as axis is provided.

16 Claims, 11 Drawing Sheets

(51) Int. Cl.
*A61M 5/158* (2006.01)
*A61M 5/162* (2006.01)
*A61M 5/38* (2006.01)
*A61M 39/10* (2006.01)
*A61M 39/28* (2006.01)
*A61M 39/22* (2006.01)

(52) U.S. Cl.
CPC .......... *A61M 5/158* (2013.01); *A61M 5/1626* (2013.01); *A61M 5/38* (2013.01); *A61M 39/10* (2013.01); *A61M 39/28* (2013.01); *A61M 2005/1402* (2013.01); *A61M 2039/229* (2013.01); *A61M 2205/6018* (2013.01); *A61M 2205/6081* (2013.01); *A61M 2209/06* (2013.01)

(58) Field of Classification Search
CPC ...... A61M 5/1414; A61M 5/158; A61M 5/38; A61M 39/10; A61M 39/28; A61J 1/10
See application file for complete search history.

(56) References Cited

FOREIGN PATENT DOCUMENTS

| | | | |
|---|---|---|---|
| JP | 2003-509163 | A | 3/2003 |
| JP | 2003-265622 | A | 9/2003 |
| JP | 2003-320029 | A | 11/2003 |
| JP | 2004-267377 | A | 9/2004 |
| JP | 2010-18539 | A | 1/2010 |
| JP | 2014-200415 | A | 10/2014 |
| WO | 2010/001939 | A1 | 1/2010 |
| WO | 2014/021390 | A1 | 2/2014 |

\* cited by examiner (a)

(b)　　　(c)

INFUSION SET

TECHNICAL FIELD

The present invention relates to an infusion set, and to an infusion set sealed within a package, which permit contamination-free priming operations while making it possible for an infusion container to be pierced on a first attempt, which make it possible to rotate and change orientation of any secondary tubing that may be connected thereto, which allow stability to be maintained during administration, and which prevent misidentification of administration procedures.

BACKGROUND ART

Medical treatments have conventionally been carried out in which therapeutic medications are formulated as infusions which are administered intravenously. Infusions employing therapeutic medications in the form of anticancer agents, nutrients, and the like must typically be administered in high dosages. Furthermore, where a plurality of medications are combined, each infusion must be administered in order, and the total administration dosage is quite high. On the other hand, as administration of infusions continues, because a sudden rise in the concentration of a drug within the blood increases the risk of occurrence of anaphylactic shock, cardiac arrhythmia, and other such side effects, there is a need for physicians and nurses to carefully continue to adjust infusion administration dose while monitoring the condition of the patient. However, carrying out administration by adjusting amount by means of injection is difficult, and as administration time goes on and the number of administrations increases, the patient experiences an increasing amount of bodily pain and is placed under an increasing amount of stress. For this reason, intravenous drip infusion is widely used as a technique for easily and continuously administering infusions to patients intravenously. During intravenous drip infusion, an infusion set is employed as medical equipment for causing a container having an infusion sealed therewithin to be connected to an intravenous drip needle that has been inserted within a blood vessel of the patient.

Infusion sets in general use conventionally employ soft tubing to link the container having the infusion sealed therewithin with the intravenous drip needle, a mechanism employing a roller clamp and a drip chamber being provided midway along said soft tubing. This is so as to make it possible to adjust the administration dosage of the infusion by causing the soft tubing to be pressed on to an appropriate degree at the roller clamp while measuring the amount of the infusion that is being delivered per unit of time at the drip chamber. In addition, infusion sets have moreover been proposed which make it possible to link a plurality of containers having infusions sealed therewithin by using a mixing region and/or Y-tubing midway along said soft tubing to split it into multiple branches to accommodate medical treatment in which a plurality of infusions are continuously administered in sequence (see Patent Reference No. 1 and Patent Reference No. 2).

The foregoing proposed infusion sets are used at the patient's bedside, a plurality of containers being linked and suspended from an IV stand. However, with such an infusion set, because the distribution of weight is upset as administration causes the amount of the infusion to decrease, there has been a risk that this can cause the IV stand to fall over, for which reason there has been a need to pay careful attention at the bedside and to, whenever required, adjust the locations from which the infusion set is suspended, as a result of which there has been a need for improvement.

Furthermore, where a plurality of anticancer agents were administered in the form of infusions, particular attention has been required to avoid mixture of solutions for which mixture is contraindicated and to see that administration is carried out in the correct order. Because the type and number of therapeutic agents are different for every patient, infusion sets must be prepared that are reassembled in correspondence thereto. However, it is often the case that the containers employed for infusions have similar external appearance. For this reason, mixups with respect to the order in which spikes pierce containers, confusion as to which infusion line should be used for different anticancer agent solutions, mistaken order of administration, and other such accidents can easily occur. Efforts have therefore been made to prevent accidents due to human errors by applying labels to the various containers at the time that the infusions are prepared, attaching written warnings, and so forth to clearly specify administration procedure, and to make the various containers recognizable, to establish standard procedures for use specific to each of the various infusion sets with their many different constitutions, to publicize this in advance, and carry out training and so forth, but the situation remains unchanged and misidentification by the operator can still occur, as a result of which there has been a need for improvement.

Furthermore, to prevent the infusion from leaking outside the blood vessel during intravenous drip infusion, it is necessary for the patient to remain as still as possible. However, because anticancer agent solutions require at least 3 to 5 hours for intravenous drip infusion, and in some cases can require extremely long times that may be as long as on the order of 48 hours, the patient will have no choice but to at some point during the course thereof go to the toilet, eat a meal, or perform some other physiological activity. The patient must therefore, while continuing to receive the intravenous drip infusion with the intravenous drip needle still stuck in his or her arm, or after closing the roller clamp and reducing the drip rate, or temporarily shutting off and interrupting the drip, or the like, move together with the IV stand, linked to which is the infusion set from which the container having the infusion sealed therewithin is suspended.

However, because the structure of conventionally proposed infusion sets has been such as to make upsetting of balance and twisting of tubing or the like unavoidable, even where the patient, physician, and nurse paid adequate attention, tension acting on the infusion set and/or intravenous drip needle has tended to cause occurrence of pain at the location where the drip infusion is inserted and/or other such bodily pain to the patient, and in the event that the intravenous drip needle that is inserted beneath the skin moved, causing anticancer agent solution to leak outside the blood vessel, or there was further tension or forcible twisting that acted thereon, there has been a risk of occurrence of accidents in which the intravenous drip needle could become dislodged from the arm of the patient, causing an extremely large amount of stress during use.

Moreover, with infusion sets employed for intravenous drip infusion, priming operations are carried out in which an infusion is used in advance to adequately remove air in advance from the soft tubing, and it is necessary to pay adequate attention to ensure that air bubbles originating from such air are not allowed to enter the patient's blood vessel. However, with such conventional infusion sets, it is sometimes the case during priming that an infusion may leak from the tip of the needle at the downstream-most end of the infusion set, and where infusions are used that employ anticancer agents or other such dangerous drugs in which powerful drugs and/or radioactive isotopes are employed, because there is a possibility that physicians and nurses could be exposed to such dangerous drugs, and moreover, that there could be occurrence of an accident in which a hospital room or a hospital wing becomes contaminated, there has been a need for a strategy to prevent such accidents.

An infusion set has therefore been proposed that adopts a strategy to reduce the likelihood of leakage of dangerous drugs to the outside environment by splitting the region upstream of the drip chamber into multiple branches to establish two switchable priming flow paths, a shutoff clamp being arranged below the drip chamber and one of the priming flow paths being employed to carry out initial priming with an infusion having a relatively low level of the dangerous drug, and the priming flow path thereafter being switched, the shutoff clamp below the drip chamber being closed, and the other priming flow path thereafter being used to carry out priming of the remaining priming flow path with an infusion having a relatively high level of the dangerous drug (see Patent Reference No. 3).

However, while it may be true that the risk of contamination during initial priming is relatively low, the structure of the foregoing proposed infusion set is such that it permits leakage of the dangerous drug from below, and so from the standpoint of whether it adequately prevents leakage of dangerous drugs to the outside environment, there has been a need for further ingenuity. Furthermore, because the structure of the foregoing proposed infusion set is such that terminal portions of the infusion set are open, operations have been complicated inasmuch as there has been a need to exercise care with respect to procedural discharge of physiological saline solution or other such solution used during priming from said terminal portions, and inasmuch as there has been a need for priming, which itself comprises multiple procedural steps, to be carried out twice, and so forth. In addition, with the foregoing proposed infusion set, even where adequate care is exercised with respect to procedural discharge of liquid, there is a risk of occurrence of damage to equipment and/or contamination of the hospital room interior as a result of unintentional spillage of the physiological saline solution that is discharged therefrom onto the infusion set, the stand, the equipment used to carry out intravenous drip infusion, and/or the floor of the hospital room, and so there has been a need for even further ingenuity.

Moreover, with the foregoing proposed infusion set, where more than two types of infusion are to be employed for intravenous drip infusion, it has been necessary to remove the container having sealed therewithin the infusion pierced by the upstream spike and to swap it for a container having the new infusion sealed therewithin, or to detach the infusion set from the intravenous drip needle and replace it with a different infusion set. However, there has been occurrence of contamination during swapping, and movement or the like of the intravenous drip needle or tension on the intravenous drip needle during swapping or replacement operations has resulted in increase in the risk that anticancer agent solution will leak outside the blood vessel. In addition, there has been occurrence of pain at the location of the drip infusion and/or increase in other such bodily pain to the patient, and there has also been increase in the likelihood of occurrence of accidents in which the intravenous drip needle moves, increasing the stress that is placed on patients, physicians, and nurses, and requiring further ingenuity and attention.

PRIOR ART REFERENCES

Patent References

Patent Reference No. 1: Japanese Patent Application Publication Kokai No. H08[1996]-336601
Patent Reference No. 2: Japanese Patent Application Publication Kokai No. 2003-265622
Patent Reference No. 3: International Patent Application Publication No. 2014/021390

SUMMARY OF INVENTION

Problem to be Solved by Invention

A problem to be solved by the present invention is to address twisting of infusion tubing and/or changes in distribution of weight of an infusion set such as may occur in accompaniment to movement of a patient, operations to add and/or replace infusion containers, or reduction in amount of liquid within infusion container(s) during intravenous drip infusion, and to provide a novel infusion set that makes it possible to easily perform operations for alleviation of twisting and operations for adjustment of position of infusion tubing and/or infusion container(s) while maintaining the stability of the infusion set, and that makes it possible to prevent bodily pain to the patient and/or leakage of liquid that might otherwise occur due to twisting and/or tension acting on the infusion set and/or the intravenous drip needle while lowering the risk of occurrence of accidents in which the IV stand from which the infusion set is suspended falls over.

Furthermore, a problem to be solved by the present invention is to, in addition to the foregoing, provide a novel infusion set that makes it possible to, by means of a simpler procedure, easily, conveniently, and definitively implement the priming and backpriming operations that are carried out prior to use of the infusion set, and in which the risk of occurrence of damage to equipment and contamination of the hospital room interior due to unintentional leakage of liquid from the infusion set while priming and backpriming operations are being carried out or after priming and backpriming operations have been carried out is drastically reduced.

In addition, a problem to be solved by the present invention is to, also in addition to the foregoing, provide a novel infusion set that makes it possible to prevent occurrence of situations in which confusion as to order of use of a plurality of spikes provided at an infusion set when installing infusion container(s) causes error in the order in which infusions are to be administered, or in which infusion(s) containing different drug(s) become mixed up among multiple pieces of infusion tubing when there has been a change in set(s) of infusion(s) at the infusion set, and other accidents such as may occur due to human error, and that makes it possible to easily establish standard procedures for use.

Means for Solving Problem

A first means in accordance with the present invention for solving the foregoing problems is an infusion set characterized in that it has a cap, for installation on a spike or a connector for connection with an intravenous drip needle, arranged at which there is an opening configured so as to not allow passage therethrough of solid or liquid but so as to allow passage therethrough of gas at the interior of the cap, a hydrophobic filter being arranged at a location inward from where the tip of the spike or the connector for connection with the intravenous drip needle is inserted at the interior of the cap by way of an insertion port for the spike or the connector for connection with the intravenous drip needle, and a lid at the exterior of said opening for closing said opening; the spike; a three-way stopcock 5 having a primary tubing downstream branch connector equipped with a mechanism that connects in such fashion as to permit rotation about primary tubing as axis; a male connector; a drip chamber; a roller clamp; the connector for connection with the intravenous drip needle; infusion tubing; a shutoff clamp for pressing on and opening and/or closing a flow path within the infusion tubing; and an optional filter bag;

wherein a spike is provided at an upstream-most location in the infusion set, said spike being connected to one end of infusion tubing equipped with a shutoff clamp for pressing on and opening and/or closing a flow path within infusion tubing, the other end of said infusion tubing being connected to a primary tubing upstream branch connector of a three-way stopcock having a primary tubing downstream branch connector equipped with a mechanism that connects in such fashion as to permit rotation about primary tubing as axis, and connected to a secondary tubing branch connector at said three-way stopcock there is one end of infusion tubing equipped with a shutoff clamp for pressing on and opening and/or closing a flow path within infusion tubing, and a spike covered with the aforesaid cap at the other end of said infusion tubing, and further connected to a primary tubing downstream branch connector of said three-way stopcock there is or are optionally one or more three-way stopcocks connected to one end of infusion tubing equipped with shutoff clamps for pressing on and opening and/or closing flow paths within infusion tubing connected to spikes covered with caps for installation on the aforesaid spikes at secondary tubing branch connectors and having primary tubing downstream branch connectors equipped with mechanisms that connect in such fashion as to permit rotation about primary tubing as axes;

wherein a male connector is further connected to a primary tubing downstream branch connector of that which among the aforesaid three-way stopcocks is disposed at a downstream location, one end of infusion tubing equipped with a shutoff clamp for pressing on and opening and/or closing a flow path within infusion tubing being further connected thereto, and a drip chamber being connected to the other end of said infusion tubing, said drip chamber being connected to one end of infusion tubing on which a roller clamp is installed, the other end of said infusion tubing being connected to a primary tubing upstream branch connector of a three-way stopcock having a primary tubing downstream branch connector equipped with a mechanism that connects in such fashion as to permit rotation about primary tubing as axis, a primary tubing downstream branch connector of said three-way stopcock being connected to a male connector, one end of infusion tubing being further connected thereto, and optionally a filter bag and infusion tubing downstream therefrom being connected to the other end of said infusion tubing, and further connected to the other end of said infusion tubing there is a primary tubing upstream branch connector of a three-way stopcock having a primary tubing downstream branch connector equipped with a mechanism that connects in such fashion as to permit rotation about primary tubing as axis, a primary tubing downstream branch connector of said three-way stopcock being connected to a male connector, one end of infusion tubing being further connected thereto, and a connector for connection with an intravenous drip needle covered with a cap for installation on the aforesaid connector for connection with an intravenous drip needle being connected to the other end of said infusion tubing.

A second means in accordance with the present invention for solving the foregoing problems is the infusion set according to the first means in accordance with the present invention characterized in that the cap, for installation on the spike, arranged at which there is the opening not permitting passage therethrough of solid or liquid but permitting passage therethrough of gas, the hydrophobic filter being arranged at the location inward from where the tip of the spike is inserted at the interior of the cap by way of the insertion port for the spike, and the lid for closing said opening at the exterior of said opening, is provided with a clip equipped with a catch for a flange disposed on the spike.

A third means in accordance with the present invention for solving the foregoing problems is the infusion set according to the first or second means in accordance with the present invention characterized in that the cap, for installation on the spike, arranged at which there is the opening not permitting passage therethrough of solid or liquid but permitting passage therethrough of gas, the hydrophobic filter being arranged at the location inward from where the tip of the spike is inserted at the interior of the cap by way of the insertion port for the spike, and the lid for closing said opening at the exterior of said opening, has a hook for anchoring said cap to infusion tubing.

A fourth means in accordance with the present invention for solving the foregoing problems is the infusion set according to any of the first through third means in accordance with the present invention characterized in that a hook for anchoring the aforesaid cap to infusion tubing has a C-shaped configuration, an O-shaped configuration, or a U-shaped configuration.

A fifth means in accordance with the present invention for solving the foregoing problems is the infusion set according to the third or fourth means in accordance with the present invention characterized in that the cap, which covers the spike, which is for installation on the spike, and arranged at which there is the opening not permitting passage therethrough of solid or liquid but permitting passage therethrough of gas, the hydrophobic filter being arranged at the location inward from where the tip of the spike is inserted at the interior of the cap by way of the insertion port for the spike, and the lid for closing said opening at the exterior of said opening, is anchored by the aforesaid hook to infusion tubing connected to the spike disposed at the upstream-most location in the infusion set.

A sixth means in accordance with the present invention for solving the foregoing problems is the infusion set according to any one of the first through fifth means in accordance with the present invention characterized in that the aforesaid three-way stopcock at which infusion tubing is connected to a secondary tubing branch connector, said infusion tubing, a shutoff clamp linked thereto, a spike, and a cap for installation on a spike are grouped together as a single group such that one or more thereamong is colored with the same color; and where there are a plurality of three-way stopcocks at which spikes are connected to secondary tubing, groups belonging to adjacent three-way stopcocks are colored so as to be respectively different colors; and colored tape of the same color is optionally applied to said infusion tubing; and a number indicating order of administration is further optionally displayed at any among the three-way stopcock, infusion tubing, shutoff clamp, spike, cap for installation on the spike, and colored tape.

A seventh means in accordance with the present invention for solving the foregoing problems is the infusion set according to the sixth means in accordance with the present invention characterized in that the aforesaid colored infusion set is further sealed within a package at which displayed in mutually offset and partially overlapping fashion on the surface thereof are a plurality of illustrations, the respective illustrations being respectively colored so as to have the same colors as the coloration given to groups within the infusion set sealed therewithin that comprise the aforesaid three-way stopcocks at which infusion tubing is connected to secondary tubing branch connectors, said infusion tubing, shutoff clamps linked thereto, spikes, and caps for installation on spikes.

An eighth means in accordance with the present invention for solving the foregoing problems is the infusion set according to the seventh means in accordance with the present invention characterized in that numbers indicating order of administration are further displayed at the aforesaid illustrations.

Benefit of the Invention

Because an infusion set in accordance with the present invention is provided in the form of an infusion set which is ready for use, there is no need for a pharmacist, physician, or nurse to assemble same in correspondence to each patient who is to be the target of medical treatment. In addition, it is possible to obtain the benefit whereby priming and backpriming are completed in extremely rapid and simple fashion by causing air within the infusion set to be quickly discharged therefrom not only at primary tubing branch(es) but also at secondary tubing branch(es), and simultaneously causing same to be filled with physiological saline solution, as a result of only a single operation in which a spike at an upstream-most location in said infusion set is inserted in an infusion container having sealed therewithin physiological saline solution which is suspended from an IV stand.

Furthermore, no physiological saline solution whatsoever is discharged from cap(s) which is/are installed at spike(s) and connector(s) for connection with intravenous drip needle(s) and at which hydrophobic filter(s) is/are arranged, and so damage to equipment and contamination do not occur. By causing said cap(s) to be provided with clip(s) equipped with catch(es) for flange(s) arranged at spike(s), the risk that cap(s) will become disengaged during priming and backpriming operations is lowered. Because lid(s) provided on cap(s) at which hydrophobic filter(s) is/are arranged are closed following priming and backpriming, physiological saline solution at regions peripheral to hydrophobic filter(s) at cap interior(s) does not spill out from cap insertion port(s). In addition, because the amount of physiological saline solution that is used can be kept to a minimum, such that an adequate remaining amount is retained therewithin, this permits effective use thereof, as there may be no need to replace the infusion container at the time of any medical treatment that may take place thereafter.

Furthermore, with an infusion set in accordance with the present invention, even where torsional forces act on infusion tubing as a result of movement of the IV stand, change in patient posture, or the like, because there are arranged at various locations a plurality of three-way stopcocks having primary tubing downstream branch connectors equipped with mechanisms that connect in such fashion as to permit rotation about primary tubing as axis or axes, it is possible by causing infusion tubing to be freely rotated where it is present below the respective three-way stopcocks for torsion to be eliminated without difficulty.

Moreover, by causing the aforesaid cap(s) to have C-shaped, U-shaped, and/or O-shaped hook(s) for anchoring same to infusion tubing, and causing said hook(s) to be anchored to infusion tubing at set(s) of primary tubing, it is possible to cause the center of gravity of the infusion set to shift toward tubing at primary tubing, making it possible to increase the stability of IV stand(s) during priming and backpriming and/or during administration of infusion(s).

As a result, no abnormal force will act on the intravenous drip needle, and the risk of occurrence of accidents in which the intravenous drip needle becomes detached or there is leakage of liquid will be greatly reduced.

In addition, at the infusion set of the present invention, three-way stopcock(s) at which infusion tubing is connected to secondary tubing branch connector(s), said infusion tubing, shutoff clamp(s) linked thereto, spike(s), and cap(s) for installation on spike(s) are grouped together as a single group such that one or more thereamong is colored with the same color. In particular, where there are a plurality of said three-way stopcocks, groups belonging to adjacent three-way stopcocks are colored so as to be respectively different colors. This makes it possible to obtain the benefit whereby an order of colors is associated with an order of administration of infusions and/or a procedure for using the infusion set, making it possible to facilitate identification of sets of secondary tubing of different groups.

Moreover, at the infusion set of the present invention, by causing the aforesaid colors and the order thereof to be adopted from those in a familiar verse or lyric of a nursery rhyme, and by moreover causing illustration(s) in which colored images associated with the aforesaid verse or lyric of a nursery rhyme based on which these were adopted to be displayed in layered fashion on a package within which the infusion set is sealed, it will be possible to naturally and accurately recognize the order of colors, i.e., the procedure for use of the infusion set and/or the order of administration of infusions, making easy memorization in association with such familiar content possible, and making it possible to more effectively prevent misidentification of administration procedures. In addition, when this is viewed by patients, nurses, and physicians, it will alleviate tension, and will make it possible to simultaneously obtain a psychological effect whereby the atmosphere at sites at which medical treatment is carried out is made more relaxing.

In addition, provision of the infusion set of the present invention will permit smooth progress to be made in standardization of operational procedures for use of the infusion set, and will make it possible to obtain the benefit whereby medical accidents such as mistaken administration or the like occurring as a result of misidentification by a pharmacist, physician, or nurse, or other such human error, are prevented.

EMBODIMENTS FOR CARRYING OUT THE INVENTION

Below, embodiments for carrying out the present invention are described as appropriate with reference to the drawings.

Configuration and Constitution of Infusion Set of Present Invention

Figure 1:
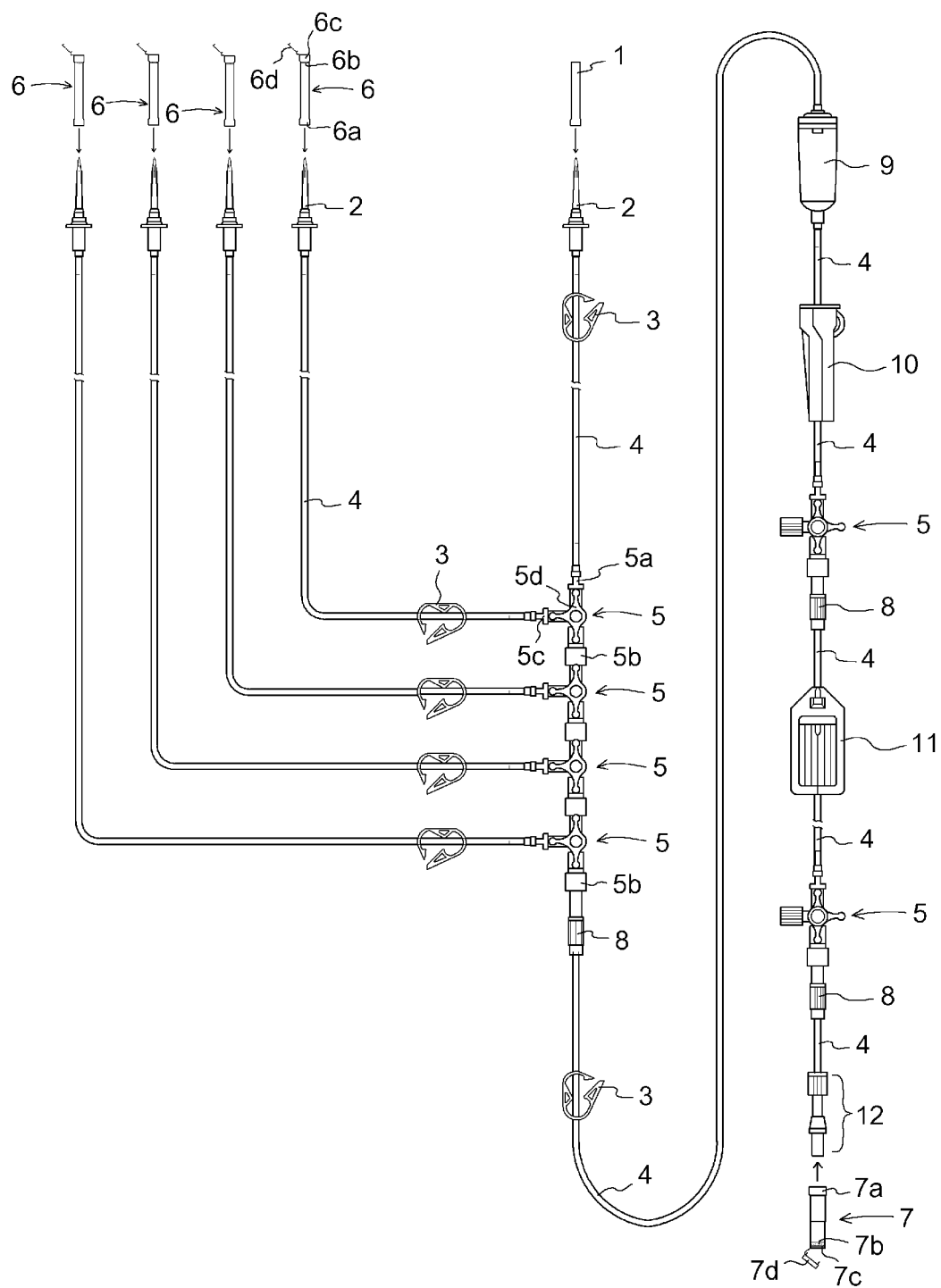
FIG. 1 Explanatory diagram showing an infusion set in accordance with the present invention.
Figure 2:
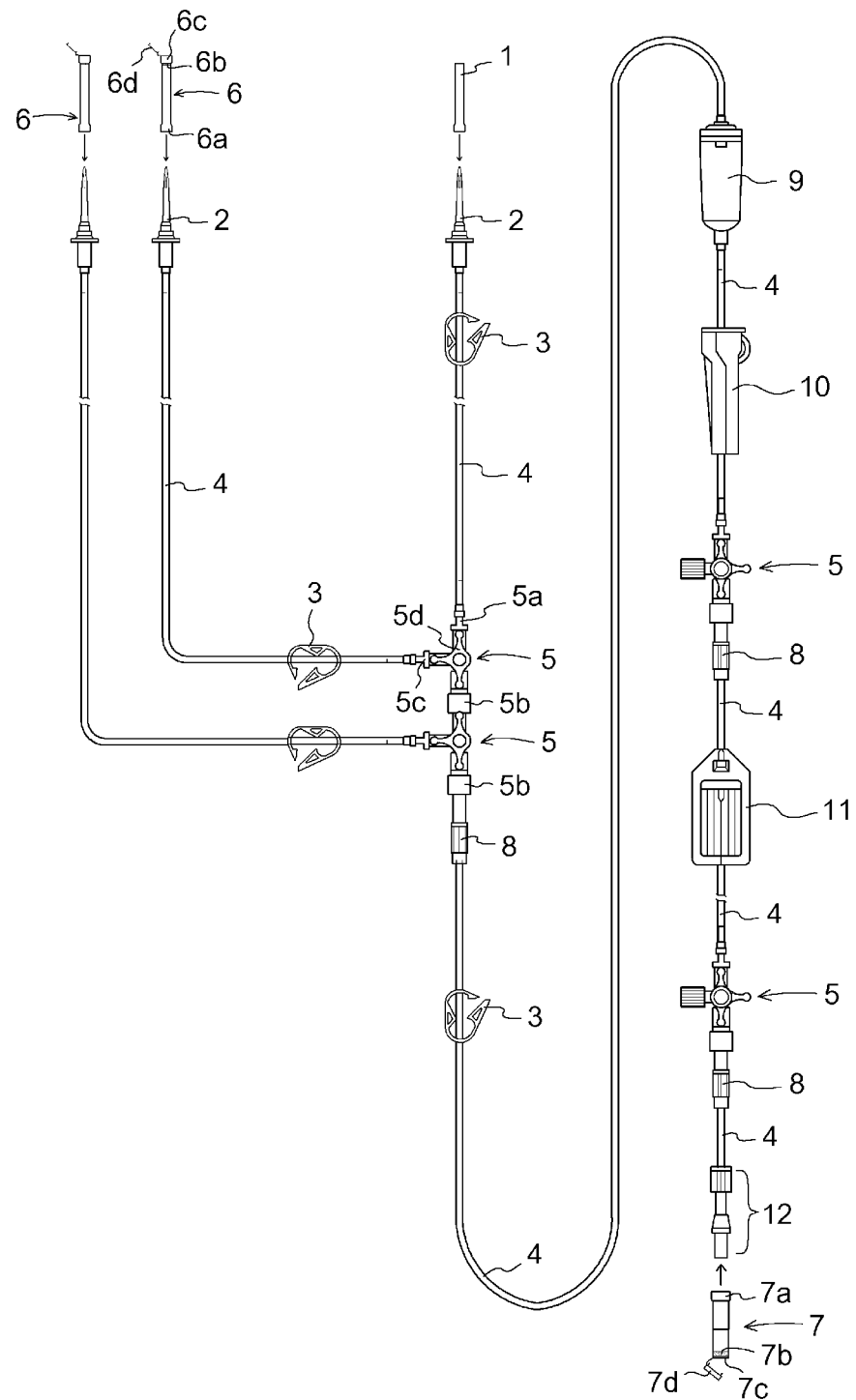
FIG. 2 Explanatory diagram showing an infusion set in accordance with the present invention.
Figure 3:
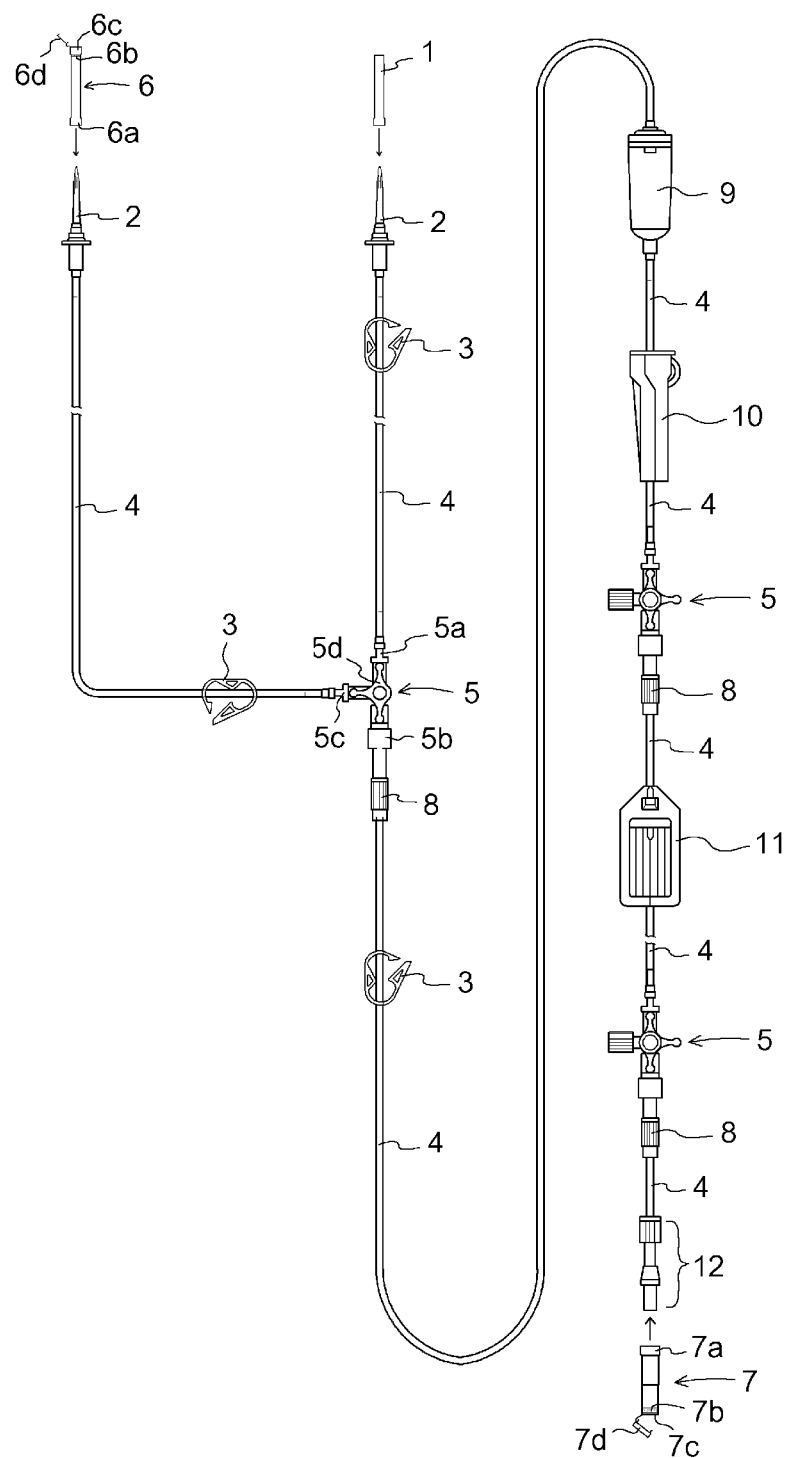
FIG. 3 Explanatory diagram showing an infusion set in accordance with the present invention.

An infusion set in accordance with the present invention has members in the form of cap(s) 6, 7 for installation on connector(s) for connection with intravenous drip needle(s) and/or spike(s), arranged at which there is/are opening(s) 6c, 7c configured so as to not allow passage therethrough of solid(s) or liquid(s) but so as to allow passage therethrough of gas(es) at interior(s) of cap(s), hydrophobic filter(s) 6b, 7b being arranged at location(s) inward from where tip(s) of connector(s) for connection with intravenous drip needle(s) and/or spike(s) is/are inserted at interior(s) of cap(s) by way of insertion port(s) 6a, 7a for connector(s) for connection with intravenous drip needle(s) and/or spike(s), and lid(s) 6d, 7d at exterior(s) of said opening(s) for closing said opening(s); spike(s) 2; three-way stopcock(s) 5 having primary tubing downstream branch connector(s) 5b equipped with mechanism(s) that connect in such fashion as to permit rotation about primary tubing as axis or axes; male connector(s) 8; drip chamber(s) 9; roller clamp(s) 10; connector(s) 12 for connection with intravenous drip needle(s); infusion tubing 4; shutoff clamp(s) 3 for pressing on and opening and/or closing flow path(s) within infusion tubing; and optional filter bag(s) 11 (FIG. 1, FIG. 2, and FIG. 3).

In addition, these respective members are connected so as to have constitution(s) as indicated below. That is, an infusion set in accordance with the present invention is equipped with spike(s) 2 at upstream-most location(s) at the infusion set, said spike(s) being connected to one end of infusion tubing 4 equipped with shutoff clamp(s) 3 for pressing on and opening and/or closing flow path(s) within infusion tubing, the other end of said infusion tubing 4 being connected to primary tubing upstream branch connector(s) 5a of three-way stopcock(s) 5 having primary tubing downstream branch connector(s) 5b equipped with mechanism(s) that connect in such fashion as to permit rotation about primary tubing as axis or axes. In addition, connected to secondary tubing branch connector(s) 5c of three-way stopcock(s) 5 there is/are one end of infusion tubing 4 equipped with shutoff clamp(s) 3 for pressing on and opening and/or closing flow path(s) within infusion tubing, and spike(s) 2 covered with the aforesaid cap(s) 6 at the other end of said infusion tubing 4. Furthermore, further connected to primary tubing downstream branch connector(s) 5b of said three-way stopcock(s) 5 there may, if desired, be one or more three-way stopcock(s) 5 connected to one end of infusion tubing 4 equipped with shutoff clamp(s) 3 for pressing on and opening and/or closing flow path(s) within infusion tubing connected to spike(s) 2 covered with cap(s) 6 for installation on the aforesaid spike(s) at secondary tubing branch connector(s) 5c and having primary tubing downstream branch connector(s) 5b equipped with mechanism(s) that connect in such fashion as to permit rotation about primary tubing as axis or axes. In addition, male connector(s) 8 is/are connected to primary tubing downstream branch connector(s) 5b of the aforesaid three-way stopcock(s) 5 disposed at downstream location(s), one end of infusion tubing 4 equipped with shutoff clamp(s) 3 for pressing on and opening and/or closing flow path(s) within infusion tubing being further connected thereto, drip chamber(s) 9 being connected to the other end of said infusion tubing 4. In addition, said drip chamber(s) 9 is/are connected to one end of infusion tubing 4 on which roller clamp(s) 10 is/are installed, the other end of said infusion tubing 4 being connected to primary tubing upstream branch connector(s) 5a of three-way stopcock(s) 5 having primary tubing downstream branch connector(s) 5b equipped with mechanism(s)

that connect in such fashion as to permit rotation about primary tubing as axis or axes. In addition, primary tubing downstream branch connector(s) 5b of said three-way stopcock(s) 5 is/are connected to male connector(s) 8, one end of infusion tubing 4 being further connected thereto, and optionally filter bag(s) 11 and infusion tubing 4 downstream therefrom being connected to the other end of said infusion tubing 4. Moreover, connected to the other end of said infusion tubing 4 there is/are primary tubing upstream branch connector(s) 5a of three-way stopcock(s) 5 having primary tubing downstream branch connector(s) 5b equipped with mechanism(s) that connect in such fashion as to permit rotation about primary tubing as axis or axes. In addition, this has a constitution such that primary tubing downstream branch connector(s) 5b of said three-way stopcock(s) 5 is/are connected to male connector(s) 8, one end of infusion tubing 4 being further connected thereto, and connector(s) 12 for connection with intravenous drip needle(s) covered with cap(s) 7 for installation on the aforesaid connector(s) for connection with intravenous drip needle(s) being connected to the other end of said infusion tubing 4. The respective members are in addition connected in advance in the form of a single integral unit which is provided as an infusion set capable of instant use (FIG. 1, FIG. 2, and FIG. 3).

Where it is necessary to remove debris or the like such as may be produced when spike(s) 2 pierce infusion container(s) 13 and/or other such solids such as may be present within infusion(s), the aforesaid filter bag(s) 11 is/are incorporated in the infusion set, and the respective members are connected in advance in the form of a single integral unit which is provided as an infusion set capable of instant use. In situations where a formulation contraindicated for use with filter bags due to the possibility that it may cause clogging is employed, in situations where no solids are present within the infusion, and in situations where a formulation having high viscosity for which it would be difficult to ensure achievement of adequate drip rate of the infusion at the time of intravenous drip infusion is employed, a constitution is employed in which said aforesaid filter bag(s) 11 is/are omitted, and the respective members are connected in advance in the form of a single integral unit which is provided as an infusion set capable of instant use.

Figure 8:
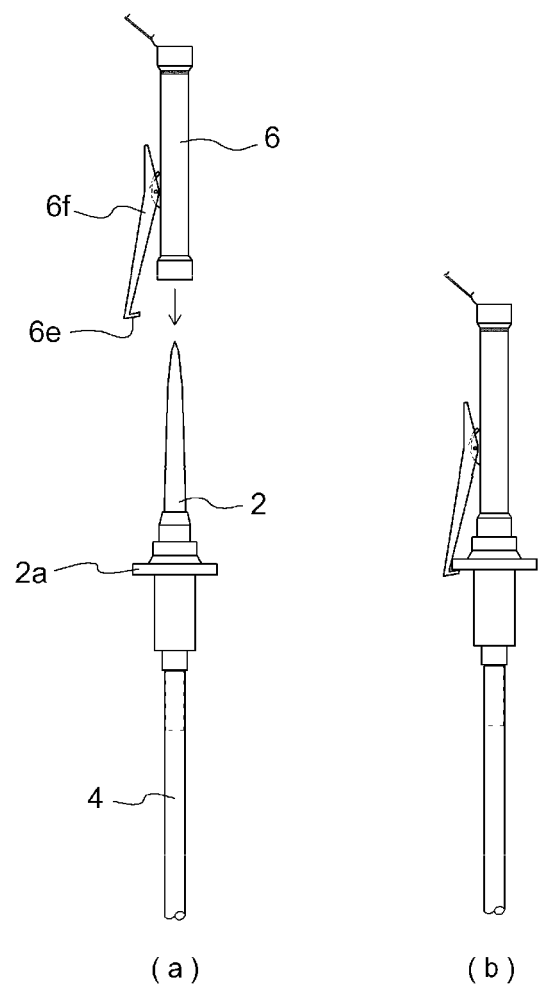
FIG. 8 Drawing for explaining a method for causing cap 6, which is employed in an infusion set in accordance with the present invention and which has clip 6f equipped with catch 6e for flange 2a arranged at spike 2, to be installed on spike 2. (a) is a drawing for explaining a situation that may exist before said cap is installed on the spike. (b) is a drawing for explaining a situation that may exist after said cap is installed on the spike.

Cap(s) 1, 6 for installation on spike(s) in the infusion set of the present invention are molded so as to mate therewith while maintaining hermiticity. In addition, said cap(s) may also be formed so as to have clip(s) 6f equipped with catch(es) for engagement with 2a provided on spike(s). Said clip(s) 6 are preferably provided on cap(s) 6 for installation on spike(s), arranged at which there is/are opening(s) not permitting passage therethrough of solid(s) or liquid(s) but permitting passage therethrough of gas(es), hydrophobic filter(s) being arranged at location(s) inward from where tip(s) of connector(s) for connection with intravenous drip needle(s) and/or spike(s) is/are inserted at interior(s) of cap(s) by way of insertion port(s) for spike(s), and lid(s) for closing said opening(s) at exterior(s) of said opening(s) (FIG. 8).

Figure 9:
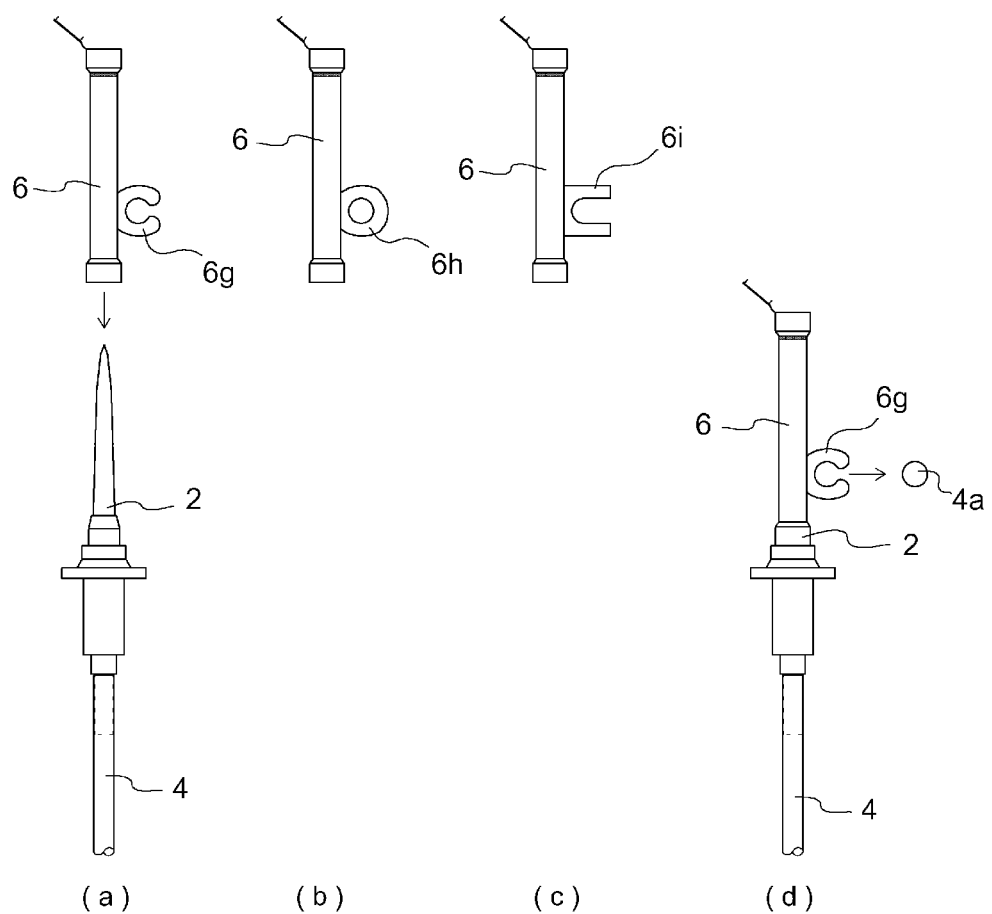
FIG. 9 Drawing for explaining a method for causing cap 6, which is employed in an infusion set in accordance with the present invention and which has a hook, to be installed on a spike 2, and for then causing this to be secured to infusion tubing. (a) is a drawing for explaining a situation that may exist before a cap which has a C-shaped hook is installed on the spike. (b) is a drawing for describing a cap which has an O-shaped hook. (c) is a drawing for describing a cap which has a U-shaped hook. (d) is a drawing for explaining a situation that may exist after a cap which has a C-shaped hook is installed on the spike.

Cap(s) 1, 6 for installation on spike(s) in the infusion set of the present invention may have hook(s) for anchoring said cap(s) to infusion tubing. Said hook(s) may preferably be hook(s) 6g of C-shaped configuration, hook(s) 6h of O-shaped configuration, and/or hook(s) 6i of U-shaped configuration ((a) at FIG. 9, (b) at FIG. 9, and (c) at FIG. 9). While said hook(s) may be arranged at any desired location(s) and orientation(s) on said cap(s), it is preferred that it or they be arranged on said cap(s) so as to cause insertion port(s) for spike(s) to be inclined upward and/or so as to cause said cap(s) to be horizontal when the aforesaid cap(s) is/are anchored to infusion tubing connected to spike(s) provided at upstream-most location(s) of the primary tubing branch. In addition, at an infusion set in accordance with the present invention, it is preferred that cap(s) having hook(s) disposed on spike(s) at the secondary tubing branch be anchored to infusion tubing connected to spike(s) provided at upstream-most location(s) of the infusion set by virtue of the aforesaid hook(s), and where there are a plurality thereof it is desirable that these be anchored in order of use from top to bottom.

In accordance with the infusion set of the present invention, three-way stopcock(s) 5 at which infusion tubing 4 is connected to secondary tubing branch connector(s) 5c, said infusion tubing 4, shutoff clamp(s) 3 linked thereto, spike(s) 2, and cap(s) 6 for installation on spike(s) may be grouped together as a single group such that one or more thereamong is colored with the same color. Moreover, where said infusion set has a plurality of three-way stopcocks 5 at which spikes 2 are connected to secondary tubing, groups belonging to adjacent three-way stopcocks 5 may be colored so as to be respectively different colors. Where coloring is carried out, respective groups are colored so as to be of different colors in correspondence to the order in which infusion(s) is/are to be administered so as to permit identification thereof.

However, despite attempts to memorize whatever unremarkable order of colors may have been established, where there is no deep meaning attached to the colors and/or order thereof, there is a risk that the colors and/or order thereof will be misidentified, for which reason particularly careful attention is demanded of nurses and physicians.

To avoid risk of misidentification, it is preferred that colors and an order thereof such as appear in a nursery rhyme, lyric, or verse that many people will know, having been familiar therewith from a young age, be employed as the colors and order thereof for identifying the aforesaid respective groups. For example, where provided in Japan, the colors and order indicated by "red, white, yellow" appearing in lyrics about tulips in the nursery rhyme might be employed; or where provided in an English-speaking region, the colors and order indicated by "red, blue, white" in the verse which goes roses are red, violets are blue, sugar is sweet, and so are you that comes from Mother Goose might be employed, respective groups being colored with different colors in order of use so as to permit identification thereof.

By thus causing an infusion set to employ coloration constituted so as to permit colors and order thereof to be memorized in association with lyrics, verses, and/or other such familiar content, as compared with memorization of an unremarkable order of colors established in the context of standardized administration procedures, nurses and physicians can more naturally and accurately recognize order of colors, i.e., procedures for use of the infusion set and/or order of administration of infusions, and as easy memorization in association with such familiar content is facilitated, it is possible to more effectively prevent misidentification of administration procedures. Moreover, this will permit smooth progress to be made in standardization of operational procedures for preventing misidentification of administration procedures at sites where many nurses and physicians are engaged in medical treatment.

In addition to the aforesaid coloration, it is possible by further optionally causing number(s) indicating order(s) of administration to be displayed at any among three-way stopcock(s), infusion tubing, shutoff clamp(s), spike(s), cap(s) for installation on spike(s), and/or colored tape(s), to even more effectively prevent misidentification of standardized administration procedures.

An infusion set provided with coloration and optionally with display of numbers indicating order of administration as described above is sealed within a pouch or other such package 15 and is provided to a site at which medical treatment is carried out. Here, to even further increase the effect whereby misidentification of standardized administration procedures may be prevented as a result of coloration and display of number(s) indicating order(s) of administration, the infusion set may be sealed within a package at which displayed in mutually offset and partially overlapping fashion on the surface thereof are a plurality of illustrations ((a) at FIG. 11). It is preferred that the infusion set be such that the foregoing illustrations are respectively colored so as to have the same colors as the coloration given to groups within the infusion set comprising the aforesaid three-way stopcocks at which infusion tubing is connected to secondary tubing branch connectors, said infusion tubing, shutoff clamps linked thereto, spikes, and caps for installation on spikes, and so as be colored in order from the frontmost illustration to the backmost illustration in correspondence to the order of use ((b) at FIG. 11). It is more preferred that the aforesaid colored illustrations be such that numbers indicating order of administration be displayed thereon in ascending order from the frontmost illustration to the backmost illustration ((c) at FIG. 11).

From frontmost to backmost, the illustrations on the aforesaid package should respectively employ, and be respectively colored, in order of appearance of images associated with a familiar verse or lyric of the nursery rhyme based on which coloration of the infusion set is carried out. By thus providing an infusion set sealed within a package displaying illustrations, nurses and physicians can, merely by looking at the package before or after the package is opened, extremely naturally and without difficulty grasp the colors and the order thereof, i.e., the order of administration, memorized in association with lyrics, verses, and/or other such familiar content, making it possible to more effectively prevent misidentification of standardized administration procedures. Moreover, by causing numbers indicating order of administration to be displayed at the respective colored illustrations, the order of use of the respective sets of infusions in the infusion set can be linked to colors and definitively recognized, making it possible to greatly reduce the likelihood of occurrence of human error.

Moreover, an infusion set sealed within a package displaying illustrations such as images associated with the aforesaid familiar verse or lyric of a nursery rhyme, when viewed by patients, nurses, and physicians will also alleviate tension, making it possible to simultaneously obtain a psychological effect whereby the atmosphere at sites at which medical treatment is carried out is made more relaxing.

Materials

There is no particular limitation with regard to the materials that may be employed for formation of the members that make up the infusion set of the present invention, it being possible to use materials such as are ordinarily employed in the context of members for infusion sets and medical equipment; for example, Nylon, polycarbonate, polypropylene, polystyrene, and/or other such resin materials and/or stainless steel and/or other such metals may be employed, it being possible to employ polyolefinic resins and/or other such materials suitable for soft tubing at the infusion tubing. Because, depending on the type of drug, e.g., anticancer agent, used, polyethylene terephthalate (PEHP) serving as plasticizer may leach from polyvinyl chloride (PVC), resin materials employed for formation of the members that make up the infusion set of the present invention do not employ polyvinyl chloride, it being preferred that these employ Nylon and/or polycarbonate. Hydrophobic filter(s) may employ polytetrafluoroethylene (PTFE), polyethylene (PE), polyolefin, polypropylene, polyethylene, polyvinylidene fluoride (PVDF), nitrocellulose, and/or the like, it being preferred that polyethylene (PE) and/or polytetrafluoroethylene (PTFE) be employed therefor. Any of the various foregoing resin materials may be employed in colored form. Furthermore, stainless steel and/or other metals may be employed in a form in which the surface thereof has undergone coloration treatment, in which case it is preferred that material(s) which have undergone coloration treatment that is highly anticorrosive be employed.

Manufacturing Operations

The infusion set of the present invention is manufactured in such fashion that the respective members are definitively connected so as to form an infusion set in the form of a single integral unit. There is no particular limitation with regard to the method for definitively connecting the respective members, it being possible to use methods such as are ordinarily employed as methods for obtaining an infusion set or medical equipment in the form of a single integral unit; for example, adhesive operations employing adhesives ordinarily used for infusion sets or other such medical equipment, fusing operations that make use of heat, ultrasonic waves, or the like, and/or other such techniques may be utilized. By providing the infusion set in the form of a single integral unit, the risk that joined parts will become separated is eliminated, making it possible to more definitively prevent medical accidents such as damage to equipment and/or contamination of the hospital room interior due to occurrence of unintentional leakage of liquid.

Moreover, so as to permit immediate commencement of priming and backpriming operations after the package has been opened and the infusion set has been removed therefrom, an infusion set in accordance with the present invention may be provided in presterilized form. There is no particular limitation with regard to the method for sterilization of the infusion set, it being possible to use methods such as are ordinarily employed as methods for sterilization of infusion sets and/or medical equipment; for example, methods which include ethylene oxide gas sterilization, γ irradiation sterilization, e-beam sterilization, radiation sterilization, ultraviolet irradiation sterilization, hydrogen peroxide sterilization, and ethanol sterilization may be employed. In addition, as said sterilization method, it is preferred based on considerations which include ease of manufacturing and cost reduction that ethylene oxide gas sterilization, e-beam sterilization, and/or γ irradiation sterilization be employed. It is preferred that e-beam sterilization be carried out to such a degree as will not cause degradation of the infusion set, and it is preferred that the irradiative energy during γ irradiation sterilization be within a range that is up to on the order of 5 kGy to 30 kGy so as to cause sterilization to be carried out to such a degree as will not cause degradation of the infusion set.

Procedure for Using Infusion Set of Present Invention

Priming and backpriming operations are first carried out on the infusion set of the present invention so as to remove air from the interior of the infusion set and cause it to be filled with physiological saline solution or other such solution.

Package 15 within which the infusion set is sealed is opened, and the infusion set is investigated to make sure that cap(s) 6 for installation on spike(s) provided with lid(s) and cap(s) 7 for installation on connector(s) for connection with intravenous drip needle(s) provided with lid(s) are definitively installed thereon, and to make sure that lid(s) 6*d*, 7*d* of the respective caps are open. Furthermore, investigation is carried out to make sure that all shutoff clamp(s) 3 are in their open state. Investigation is carried out to make sure that lever(s) 5*d* of three-way stopcock(s) at which infusion tubing connected to spike(s) is/are connected at secondary tubing branch(es) is/are in position(s) permitting flow to/from all three branches, and to make sure that lever(s) 5*d* of three-way stopcock(s) for use as emergency port(s) at which there is no spike or infusion tubing connected at secondary tubing branch(es) is/are in position(s) permitting flow to/from primary tubing upstream branch(es) and primary tubing downstream branch(es) but not permitting flow to/from secondary tubing branch(es). Furthermore, investigation is carried out to make sure that roller clamp(s) 3 are in their open state (FIG. 5, (a) at FIG. 6, (b) at FIG. 6).

Figure 5:
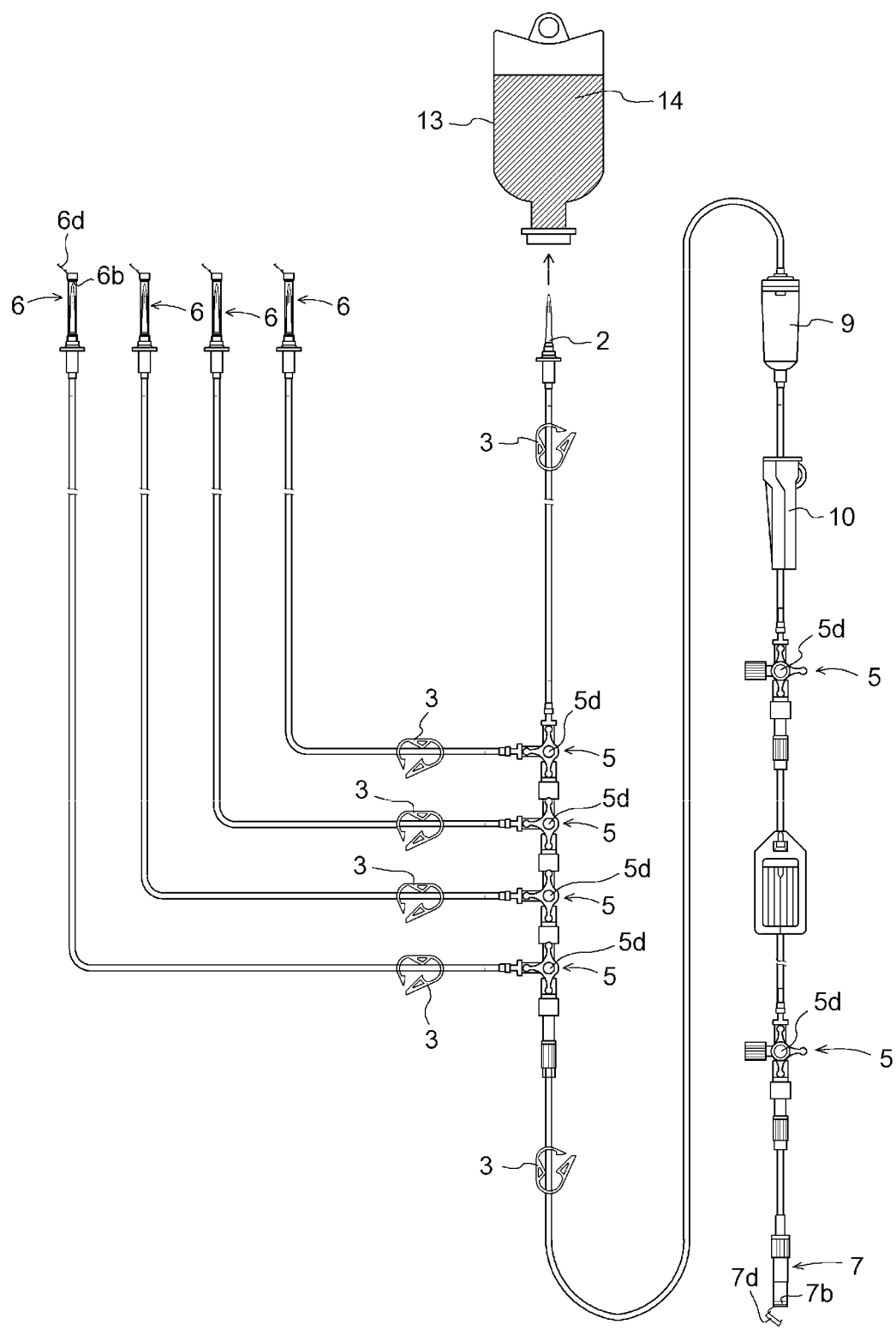
FIG. 5 Drawing for explaining a method for carrying out priming and backpriming in the context of an infusion set in accordance with the present invention.

Next, infusion container 13 having sealed therewithin physiological saline solution 14 for use during priming and backpriming is suspended from an IV stand. In addition, cap 1 which is for installation on a spike and which is installed on the spike 2 disposed at the upstream-most location in the infusion set of the present invention is removed, the seal of said infusion container 13 suspended from the IV stand is pierced with spike 2 disposed at the upstream-most location in the infusion set, and priming and backpriming operations are initiated (FIG. 5). Where the IV stand is equipped with a stay rod for securing drip chamber 9 or other such securing hardware, this may be used to secure the foregoing. Note that it is preferred even where securing is not carried out during priming and backpriming that securing hardware be used to secure drip chamber 9 when initiating intravenous drip infusion, to prevent the entire weight of the infusion set from being borne by intravenous drip needle(s) and connector(s) 12 for connection with intravenous drip needle(s), so that region(s) at which intravenous drip needle(s) are inserted are not placed under stress.

Physiological saline solution 14 flows into infusion tubing 4 from infusion container 13 placed on spike 2 disposed at the upstream-most location, and priming operations commence. As physiological saline solution 14 displaces air within infusion tubing 14, it flows from primary tubing upstream branch connector 5*a* of the three-way stopcock 5 which is disposed downstream therefrom into three-way stopcock 5. Because lever 5*d* of said three-way stopcock 5 is positioned so as to permit flow to/from all three branches, as physiological saline solution 14 flowing thereinto displaces air within three-way stopcock 5, it further flows into primary tubing downstream branch connector 5*b* which is equipped with a mechanism that connects in such fashion as to permit rotation about the primary tubing as axis and secondary tubing branch connector 5*c* of the three-way stopcock.

Furthermore, physiological saline solution 14 that has flowed into secondary tubing branch connector 5*c* of the aforesaid three-way stopcock, being physiological saline solution for carrying out backpriming, as it displaces air within infusion tubing 4 which is further connected thereto, flows into spike 2 which is connected at the far side thereof. After flowing thereinto, physiological saline solution 14, as it displaces air within spike 2, flows from the tip of said spike 2 into the interior of cap 6 which is for installation on a spike and which is installed on said spike, arranged at which there is an opening not permitting passage therethrough of liquid(s) or solid(s) but permitting passage therethrough of gas(es) at the interior of the cap, a hydrophobic filter being arranged at a location inward from where the tip of the spike is inserted at the interior of the cap by way of the insertion port for the spike, and a lid for closing said opening at the exterior of said opening. In addition, air that had been present in the region from the periphery at the tip of the spike to the interior sidewall of the cap at hydrophobic filter 6*b* is displaced therefrom by physiological saline solution 14 which flows thereinto, passes through hydrophobic filter 6*b*, and is discharged to the exterior by way of cap opening 6*c*, as a result of which that portion becomes filled with physiological saline solution 14. Here, hydrophobic filter 6*b* does not permit passage therethrough of physiological saline solution 14. Furthermore, air remains in the portion toward the base from the tip of spike 2 from which physiological saline solution 14 flows at the cap interior ((c) at FIG. 6).

On the other hand, physiological saline solution 14 which has flowed into the interior of primary tubing downstream branch connector 5*b* equipped with a mechanism that connects in such fashion as to permit rotation about the primary tubing as axis at the aforesaid three-way stopcock 5 further displaces air from within infusion tubing 4 connected thereto to a location downstream therefrom.

In the event that three-way stopcock(s) 5 is/are further connected at the far end of said infusion tubing 4, physiological saline solution 14 that has flowed thereinto, being physiological saline solution 14 for carrying out backpriming, further flows in order, in the same fashion as has been described above, into secondary tubing branch connector(s) 5*c* of three-way stopcock(s), interior(s) of infusion tubing 4, interior(s) of spike(s) 2, and interior(s) of cap(s) 6, installed on said spike(s), which is/are for installation on spike(s), arranged at which there is/are opening(s) not permitting passage therethrough of liquid(s) or solid(s) but permitting passage therethrough of gas(es) at interior of cap(s), hydrophobic filter(s) being arranged at location(s) inward from where tip(s) of spike(s) is/are inserted at interior of cap(s) by way of insertion port(s) for spike(s), and lid(s) for closing said opening(s) at exterior(s) of said opening(s). In addition, physiological saline solution 14 which flows thereinto causes air present in the region from the periphery at the tip of the spike into which physiological saline solution 14 flows to the interior sidewall of the cap at hydrophobic filter 6 to pass through the hydrophobic filter and to be displaced to the exterior by way of the cap opening, as a result of which that portion becomes filled with physiological saline solution. Here, hydrophobic filter 6 does not permit passage therethrough of physiological saline solution 14. Furthermore, air remains in the portion toward the base from the tip of spike 2 from which physiological saline solution 14 flows at the interior of cap 6.

In addition, physiological saline solution 14 which has flowed into the interior of primary tubing downstream branch connector 5*b* equipped with a mechanism that connects in such fashion as to permit rotation about the primary tubing as axis at the aforesaid three-way stopcock 5 displaces air from within infusion tubing 4 further connected thereto to a location downstream therefrom, and in so doing causes it to flow into drip chamber 9 which is connected at the far end thereof. As physiological saline solution 14 which has flowed thereinto displaces air from within infusion tubing 4 further connected thereto to a location downstream therefrom, it flows into the interior of three-way stopcock 5 and filter bag 11 which are connected at the far end thereof, and as it displaces air from within infusion tubing 4 further connected thereto to a location downstream therefrom, it flows therealong to flow into connector 12 for connection with an intravenous drip needle.

After flowing into connector 12 for connection with an intravenous drip needle, physiological saline solution 14, as it displaces the air therewithin to a location downstream therefrom, flows from the tip of connector 12 for connection with an intravenous drip needle into the interior of cap 7 which is for installation on a connector for connection with an intravenous drip needle, arranged at which there is an opening not permitting passage therethrough of liquid(s) or solid(s) but permitting passage therethrough of gas(es) at the interior of the cap, a hydrophobic filter being arranged at a location inward from where the tip of the connector for connection with an intravenous drip needle is inserted at the interior of the cap by way of the insertion port for the connector for connection with an intravenous drip needle, and a lid for closing said opening at the exterior of said opening. In addition, physiological saline solution 14 which has flowed thereinto causes air that had been present in the region peripheral thereto to further pass through hydrophobic filter 7b and to be displaced to the exterior by way of cap opening 7c, as a result of which the region peripheral thereto becomes filled with physiological saline solution 14. Here, hydrophobic filter 7b does not permit passage therethrough of physiological saline solution 14. Furthermore, air remains in the portion toward the base from the tip of connector 12 for connection with an intravenous drip needle from which physiological saline solution 14 flows at the interior of cap 7.

Figure 7:
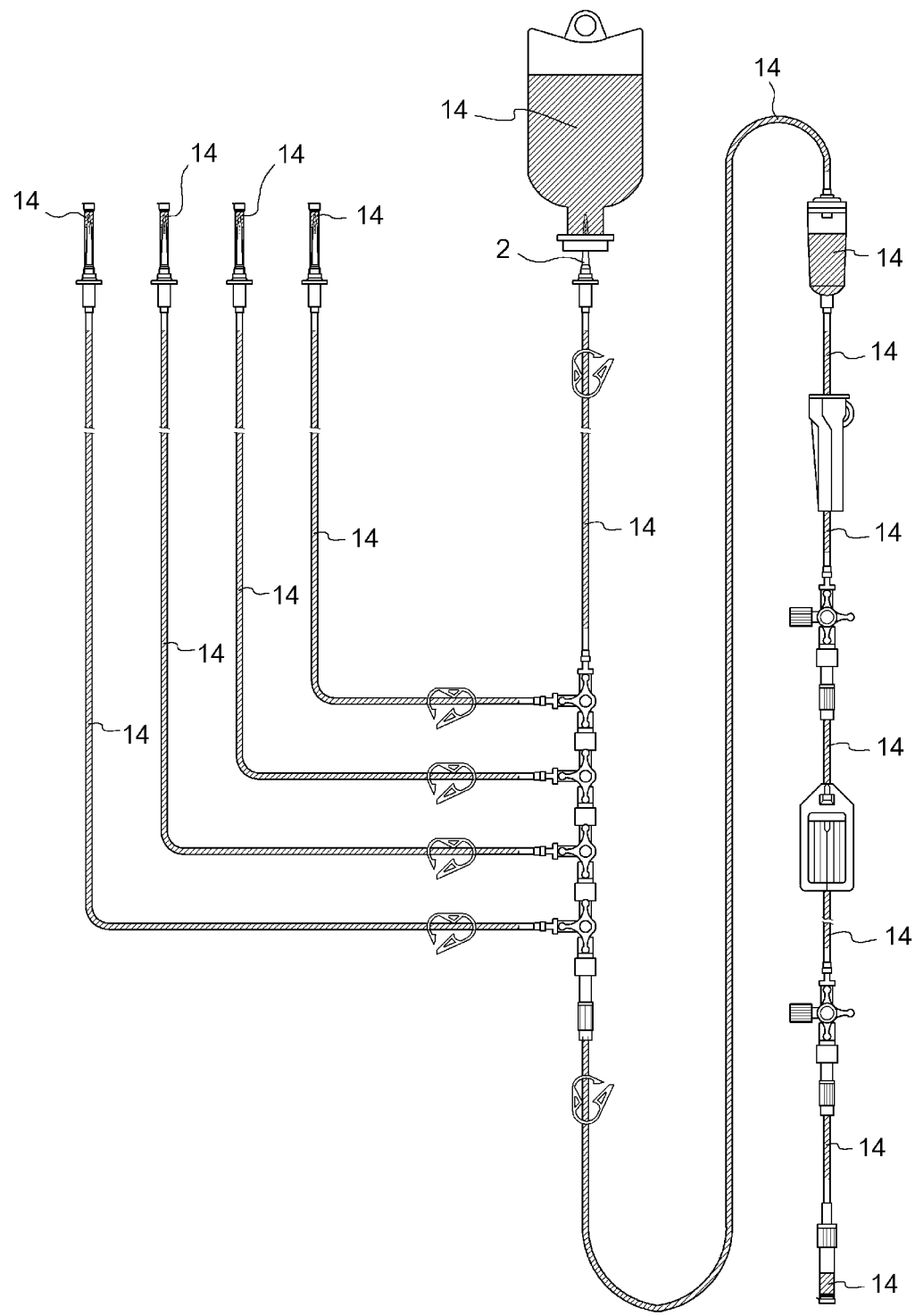
FIG. 7 Drawing for explaining a situation that may exist when priming and backpriming have been completed, and lids 6d, 7d at caps 6, 7 have been closed, in the context of an infusion set in accordance with the present invention.

In this way, at an infusion set in accordance with the present invention, priming and backpriming are completed not only at primary tubing branch(es) but also at secondary tubing branch(es) by causing air within said infusion set to be quickly discharged therefrom and simultaneously causing said infusion set to be filled with physiological saline solution as a result of only a single operation in which "a spike 2 disposed at an upstream-most location in said infusion set is inserted in an infusion container 13 which has sealed therewithin physiological saline solution 14 for use during priming and backpriming and which is suspended from an IV stand" (FIG. 7). Furthermore, even where there are a plurality of linked three-way stopcocks with a plurality of sets of secondary tubing being provided thereat, at an infusion set in accordance with the present invention, priming and backpriming are completed in the same manner as described above not only at the primary tubing branch but also at the plurality of secondary tubing branches by causing air within said infusion set to be quickly discharged therefrom and simultaneously causing the interiors to be filled with physiological saline solution as a result of only the aforesaid single operation (FIG. 7). In addition, regardless of which of the foregoing situations applies, because hydrophobic filter(s) 6b, 7b is/are present at cap(s) 6 installed on spike(s) and at cap(s) 7 installed on connector(s) for connection with intravenous drip needle(s), there will be no occurrence of leakage of liquid even if lid(s) is/are open.

During the aforesaid priming and backpriming operations, because hydrophobic filter(s) 6b, 7b is/are present, there will be absolutely no discharge of unwanted liquid, and there will be no occurrence of damage to equipment and/or contamination of the hospital room interior. Moreover, because the amount of the physiological saline solution sealed within the infusion container connected to the spike at the upstream-most location that is used can be kept to a minimum, such that an adequate remaining amount is retained therewithin, this permits effective use thereof, as there may be no need to replace the infusion container at the time of medical treatment that may take place thereafter. Furthermore, because an infusion set in accordance with the present invention is assembled in advance in the form of a single integral unit, there being no occurrence of unintentional leakage of liquid during priming and backpriming operations, there will be no occurrence of damage to equipment and/or contamination of the hospital room interior.

Figure 6:
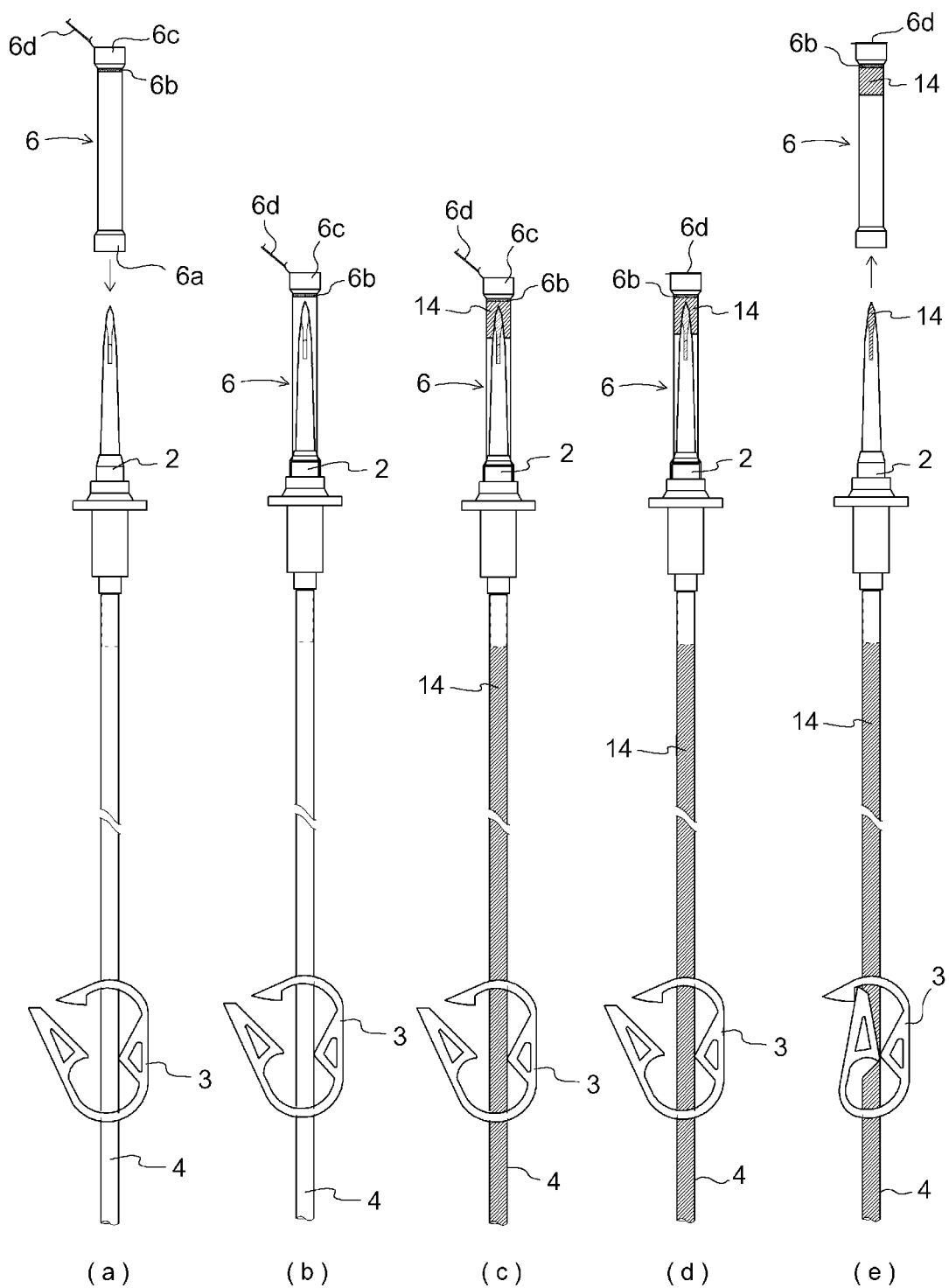
FIG. 6 Drawing for explaining a situation that may exist when carrying out backpriming in the context of an infusion set in accordance with the present invention. (a) is a drawing for explaining a situation that may exist before cap 6 for installation on a spike is installed on spike 2. (b) is a drawing for explaining a situation that may exist when cap 6 for installation on a spike is installed on spike 2. (c) is a drawing for explaining a situation that may exist when backpriming is initiated, at which time physiological saline solution 14 enters infusion tubing 4, spike 2, and the interior of cap 6 for installation on a spike. (d) is a drawing for explaining a situation that may exist when lid 6d at said cap is shut after backpriming has been completed. (e) is a drawing for explaining a method employed when cap 6, the lid 6d at which is shut, is removed from spike 2 after backpriming has been completed.

After completion of priming and backpriming, lid(s) 6d, 7d at cap(s) for installation on spike(s) and at cap(s) for installation on connector(s) for connection with intravenous drip needle(s) are closed ((d) at FIG. 6, FIG. 7). In addition, shutoff clamp(s) 3 disposed at respective set(s) of infusion tubing 4 is/are pinched together, and roller clamp(s) 10 is/are moved to their closed position(s), to close off the respective set(s) of infusion tubing 4. Furthermore, lever(s) 5d at three-way stopcock(s) 5 is/are moved to position(s) corresponding to the intravenous drip infusion(s) to be initiated.

Cap(s) 6 is/are removed from where it/they is/are installed on spike(s) 2 to which therapeutic agent(s) is/are connected (also see (e) at FIG. 6). Furthermore, cap(s) 7 is/are removed from where it/they is/are installed on connector(s) 12 for connection with intravenous drip needle(s). Said spike 2 is made to pierce infusion container 13 within which a therapeutic solution is sealed, and connector 12 for connection with an intravenous drip needle is connected to an intravenous drip needle. Notwithstanding that the foregoing operations are carried out, because tubing at the infusion set has been placed in its closed state, there is no leakage of physiological saline solution 14 used for priming and backpriming from spike(s) 2 or connector(s) 12 for connection with intravenous drip needle(s) removed therefrom, and there is no occurrence of damage to equipment and/or contamination of the hospital room interior. Furthermore, because lid(s) is/are shut at the aforesaid cap(s) 6, 7, air does not flow thereinto and there is no air that again passes therethrough from hydrophobic filter(s) 6b, 7b, and moreover, surface tension due to the physiological saline solution and atmospheric pressure from opening(s) 6c, 7c at the cap(s) act in such fashion that physiological saline solution 14 at region(s) peripheral to hydrophobic filter(s) at the interior does not spill out from insertion port(s) 6a, 7a at cap(s), and there is no occurrence of damage to equipment and/or contamination of the hospital room interior (see also (e) at FIG. 6).

Where a plurality of infusion sets are used, there is a need to prevent accidents in which intravenous drip needle(s) become detached or there is leakage of liquid from region(s) at which intravenous drip needle(s) are inserted due to application of torsional forces on infusion tubing or accidents in which IV stand(s) fall over due to changes in the distribution of weight. Furthermore, where an anticancer agent or the like is administered by intravenous drip infusion, because particularly long times are required, there is a need to accommodate the fact that the patient will move about and to implement measures to prevent accidents of the same type as described above.

Figure 4:
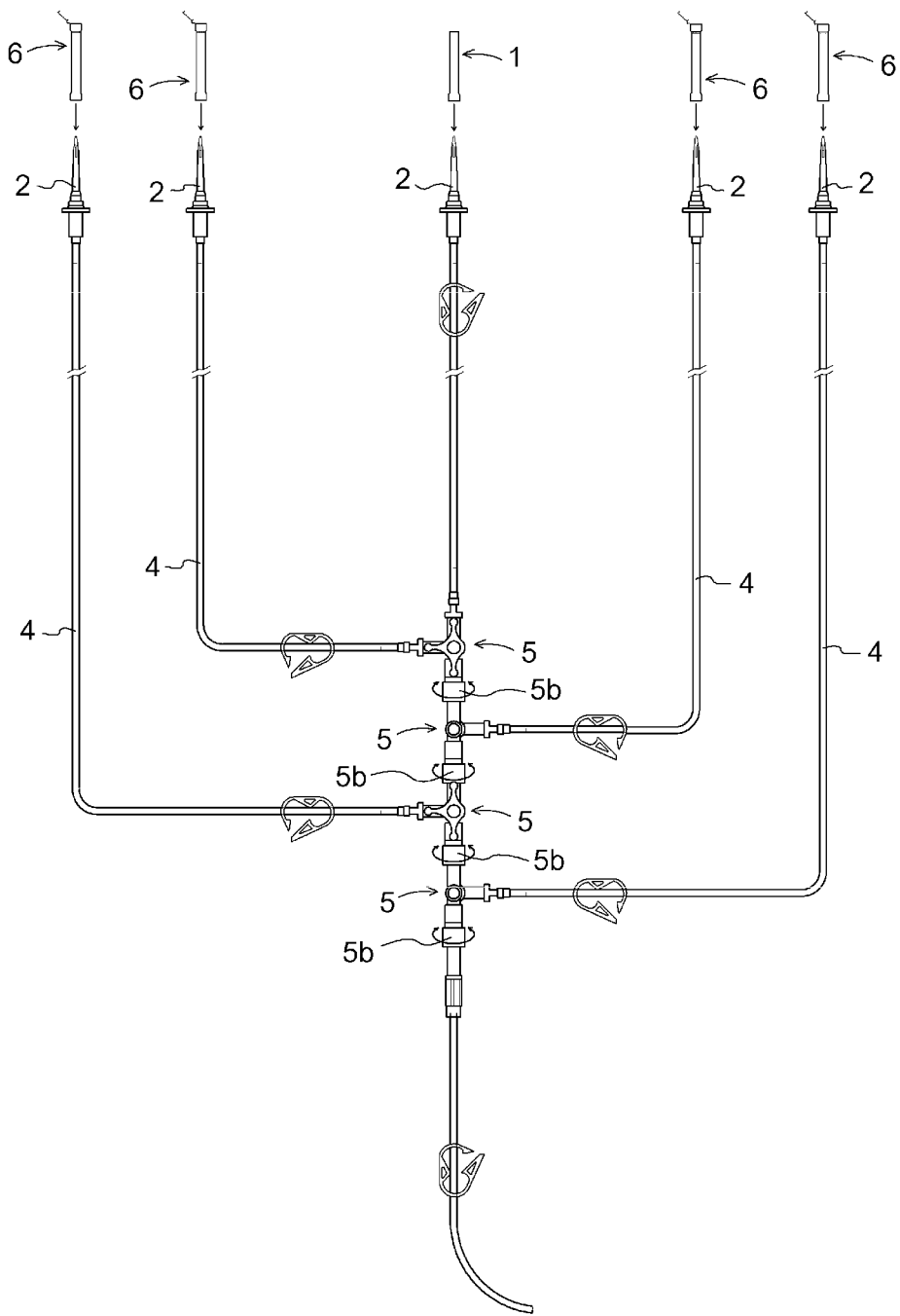
FIG. 4 Explanatory diagram showing rotation of primary tubing downstream branch connectors at three-way stopcocks in an infusion set in accordance with the present invention.

To address the foregoing needs, because an infusion set in accordance with the present invention employs three-way stopcock(s) in the form of three-way stopcock(s) 5 having primary tubing downstream branch connector(s) 5b equipped with mechanism(s) that connect in such fashion as to permit rotation about primary tubing as axis or axes, even where a plurality of infusion containers 13 within which therapeutic solutions are sealed are employed, by freely rotating member(s) downstream from said primary tubing downstream branch connector(s) 5*b* in the infusion set, it will be possible for balance to be maintained (FIG. 4).

In particular, an infusion set in accordance with the present invention may be such that a plurality of three-way stopcocks 5 having primary tubing downstream branch connectors 5*b* equipped with mechanisms that connect in such fashion as to permit rotation about primary tubing as axis or axes are further arranged below drip chamber 9 (FIG. 1, FIG. 2). And, when being used to administer an intravenous drip infusion, change(s) in only the location(s) of infusion container(s) 13 can be made to occur by freely rotating region(s) above three-way stopcock(s) 5 for use as emergency port(s) arranged below drip chamber 9, and below said primary tubing downstream branch connector(s) 5*b*, in the infusion set. By so doing, because it will be only the region above the three-way stopcock arranged below drip chamber 9 that rotates, it being possible for this to be accomplished without the need to rotate the tubing below said three-way stopcock, no abnormal force will act on the intravenous drip needle, and the risk of occurrence of accidents in which the intravenous drip needle becomes detached or there is leakage of liquid will be greatly reduced.

Moreover, during use of an infusion set in accordance with the present invention, even where torsional forces act on infusion tubing as a result of movement of the IV stand, change in patient posture, or the like, because in an infusion set in accordance with the present invention there are arranged at various locations a plurality of three-way stopcocks 5 having primary tubing downstream branch connectors 5*b* equipped with mechanisms that connect in such fashion as to permit rotation about primary tubing as axis or axes, infusion tubing can be freely rotated where it is present below the respective three-way stopcocks, permitting torsion to be eliminated without difficulty. As a result, no abnormal force will act on the intravenous drip needle, and the risk of occurrence of accidents in which the intravenous drip needle becomes detached or there is leakage of liquid will be greatly reduced.

Where an infusion set in accordance with the present invention is used to administer an intravenous drip infusion, the infusion may be allowed to drip under the influence of gravity with drip rate being adjusted by drip chamber 9 and roller clamp 10, or drip chamber 9 may be further combined with an infusion monitor for adjustment of drip rate. In addition, drip chamber 9 and/or the infusion monitor are secured to a securing stay rod or other such securing hardware with which the IV stand is equipped so as to prevent the entire weight of the infusion set from being borne by intravenous drip needle(s) and connector(s) 12 for connection with intravenous drip needle(s). Furthermore, an infusion pump may be further combined therewith for adjustment of drip rate. This is useful at times when flow rate is low due to use of filter bag(s) 11 or use of therapeutic infusion(s) having high viscosity. Even where heavy infusion monitor(s) and infusion pump(s) are used in combination, by freely rotating the region(s) below a plurality of three-way stopcocks 5 having primary tubing downstream branch connectors 5*b* equipped with mechanisms that connect in such fashion as to permit rotation about primary tubing as axis or axes which are arranged at various locations in an infusion set in accordance with the present invention, adjustment of balance and elimination of torsion at tubing can be easily carried out. As a result, no abnormal force will act on the intravenous drip needle, and the risk of occurrence of accidents in which the intravenous drip needle becomes detached or there is leakage of liquid will be greatly reduced.

Furthermore, in accordance with another aspect of the present invention, cap 6 for installation on the aforesaid spike, to prevent untimely detachment during priming and backpriming operations, has clip(s) 6*f* equipped with catch(es) 6*e* for engagement with flange(s) 2*a* provided on spike 2. During use, catch 6*e* of clip 6*f* which is present on cap 6 is secured by causing it to engage with flange 2*a* provided on spike 2 ((a) at FIG. 8, (b) at FIG. 8).

Moreover, in accordance with another aspect of the present invention, cap 6 for installation on the aforesaid spike is equipped with hook(s) for anchoring said cap to infusion tubing. Where the cap has C-shaped hook 6*g* and/or U-shaped hook 6*i*, infusion tubing 4 is secured by causing it to be squeezed at the desired location(s) within the C-shaped and/or U-shaped portion(s) of said hook(s) (see also (a) at FIG. 9, (b) at FIG. 9, and (d) at FIG. 9). Where O-shaped hook(s) 6*h* is/are employed, because infusion tubing is made to pass through the O-shaped hole(s) of the hook(s) at the time of manufacturing, securing is accomplished by moving the hook(s) to the desired location(s) (see also (b) at FIG. 9). Cap(s) 6 equipped with hook(s) is/are secured to infusion tubing 4 at primary tubing branch(es). Where there are a plurality of sets of secondary tubing due to the fact that there are a plurality of linked three-way stopcocks 5, caps 6 equipped with respective hooks might be secured to infusion tubing 4 at primary tubing branches. Moreover, infusion tubing may optionally be organized by bundling tubing together with paper tape or the like. By securing these as described above, center(s) of gravity of infusion line(s) connected to secondary tubing branch(es) and cap(s) 6 is/are made to shift toward primary tubing branch(es), increasing stability of IV stand(s) during priming and backpriming, during administration of infusion(s), and so forth.

By using cap(s) 6 equipped with hook(s) as described above, because cap(s) may be left anchored to infusion tubing, it is possible to become free of the risks of damage to equipment and contamination of the hospital room interior that can occur due to splattering of physiological saline solution remaining in cap interior(s) when cap(s) that have been removed slip from the fingers or is/are otherwise allowed to fall following backpriming.

Figure 10:
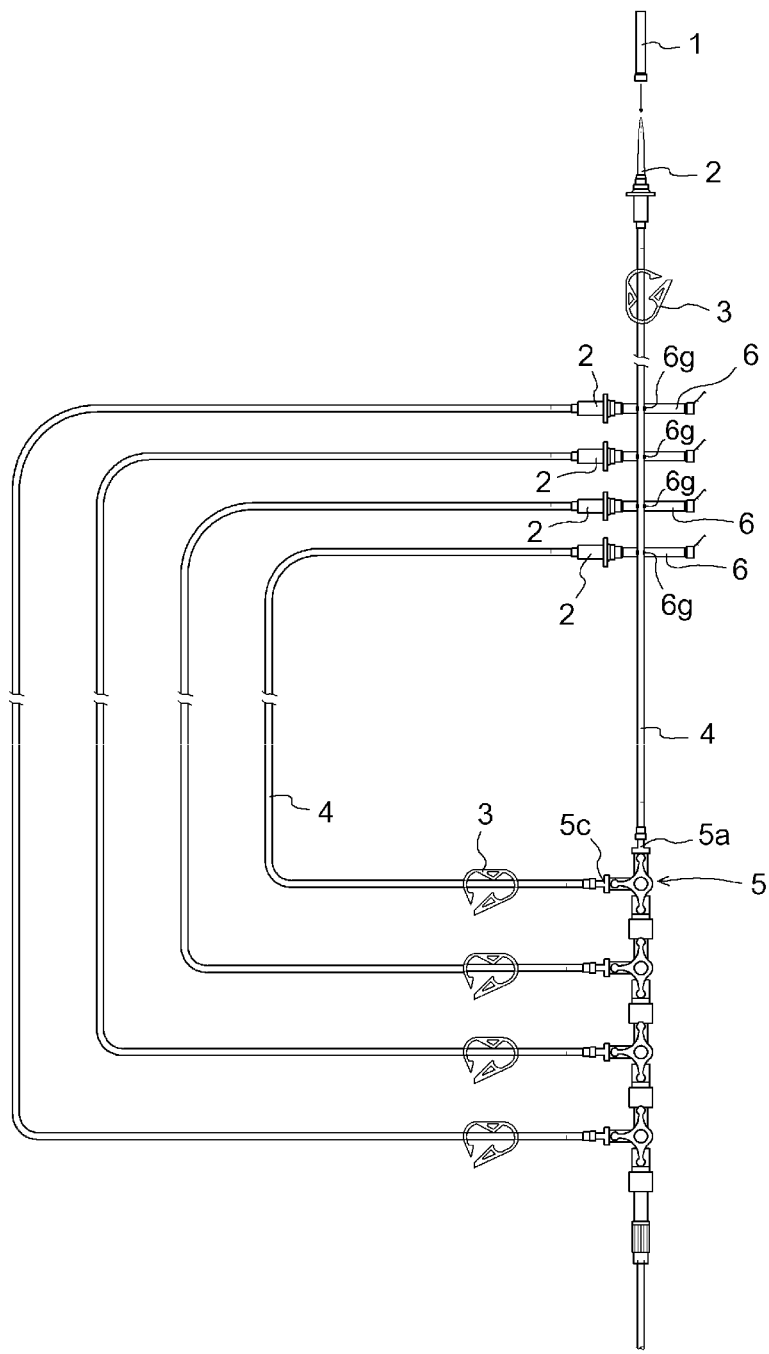
FIG. 10 Drawing for explaining a situation that may exist when spike 2, on which cap 6 that has a hook is installed, is secured in horizontal fashion to infusion tubing in the context of an infusion set in accordance with the present invention.

Furthermore, where there are a plurality of sets of secondary tubing due to the fact that there are a plurality of linked three-way stopcocks 5, it is necessary that adequate attention be paid so as not to confuse the order of use of secondary tubing. In particular, where an anticancer agent or other such drug contraindicated for mixture with different drug(s) is being used, it will be necessary to first use the secondary tubing set connected to the downstream three-way stopcock and to thereafter use the secondary tubing set(s) connected to three-way stopcock(s) upstream therefrom in sequence. Here, caps 6 equipped with respective hooks are secured to infusion tubing 4 at primary tubing branches in stacked fashion in the order in which they will be used (FIG. 10). By so doing, it will be possible, without misidentification of sequence, to definitively select the secondary tubing branch tubing that should be used, making it possible to become free of the risk of occurrence of human error.

WORKING EXAMPLES

Indicated below are working examples of manufacture and use of infusion sets in accordance with the present invention. The present invention is not to be limited in any way by these descriptions.

Members for constructing an infusion set in accordance with the present invention were prepared in the form of a cap, for installation on a spike, arranged at which there was an opening configured so as to not allow passage therethrough of solid or liquid but so as to allow passage therethrough of gas at the interior of the cap, a hydrophobic filter being arranged at a location inward from where the tip of the spike was inserted at the interior of the cap by way of an insertion port for the spike, and a lid at the exterior of said opening for closing said opening; a spike; a three-way stopcock having a primary tubing downstream branch connector equipped with a mechanism that connected in such fashion as to permit rotation about primary tubing as axis; a male connector; a drip chamber; a roller clamp; a connector for connection with an intravenous drip needle; infusion tubing; a shutoff clamp for pressing on and opening and/or closing flow path(s) within infusion tubing; an optional filter bag; and a cap, for installation on a connector for connection with an intravenous drip needle, arranged at which there was an opening configured so as to not allow passage therethrough of solid or liquid but so as to allow passage therethrough of gas at the interior of the cap, a hydrophobic filter being arranged at a location inward from where the tip of the connector for connection with the intravenous drip needle was inserted at the interior of the cap by way of an insertion port for the connector for connection with the intravenous drip needle, and a lid at the exterior of said opening for closing said opening.

The foregoing members were connected to form of a single integral unit as described at the section entitled Configuration and Constitution of Infusion Set of Present Invention and the section entitled Manufacturing Operations. In addition, caps for installation on spikes provided with lids and caps for installation on connectors for connection with intravenous drip needles provided with lids were definitively installed thereon, lids of the respective caps were opened, all shutoff clamps were placed in their open states, levers of three-way stopcocks at which infusion tubing connected to spikes were connected at secondary tubing branches were moved to positions permitting flow to/from all three branches, levers of three-way stopcocks for use as emergency ports at which there were no spikes or infusion tubing connected at secondary tubing branches were moved to positions permitting flow to/from primary tubing upstream branches and primary tubing downstream branches but not permitting flow to/from secondary tubing branches, and roller clamp 3 was placed in its open state, to manufacture an infusion set in accordance with the present invention. As shown in FIG. 1, an infusion set equipped with four sets of secondary tubing was manufactured as Working Example 1.

As shown in FIG. 1, an infusion set equipped with four sets of secondary tubing was manufactured as Working Example 1.

As Working Example 2, an infusion set in which, instead of the caps having hydrophobic filters for installation on spikes employed at Working Example 1, members were employed which were such that clips equipped with catches for flanges of spikes were further provided on said caps, but which in other respects was identical to Working Example 1, was manufactured.

As Working Example 3, an infusion set in which, instead of the caps having hydrophobic filters for installation on spikes employed at Working Example 1, members were employed which were such that hooks of C-shaped configuration for anchoring to infusion tubing were provided on said caps, the caps being anchored to infusion tubing as shown in FIG. 10, but which in other respects was identical to Working Example 1, was manufactured.

As Working Example 4, an infusion set which had three three-way stopcocks having infusion tubing at secondary tubing branches, and which employed shutoff clamps with which the secondary tubing branches were equipped that, starting from the bottom, were respectively colored in order so as to be red, white, and yellow, but which in other respects was identical to Working Example 1, was manufactured.

Figure 11:
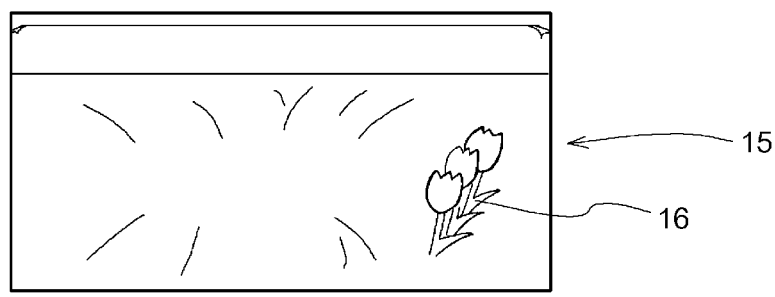
FIG. 11 Drawing for explaining an infusion set in accordance with the present invention that is sealed within a package at which displayed in mutually offset and partially overlapping fashion on the surface thereof are a plurality of illustrations 16. (a) is an explanatory diagram showing the external appearance of a package. (b) is a drawing for explaining the coloration that is applied to the illustrations. (c) is a drawing for explaining numbers indicating order of administration that are further displayed on the illustrations.
Figure 11:
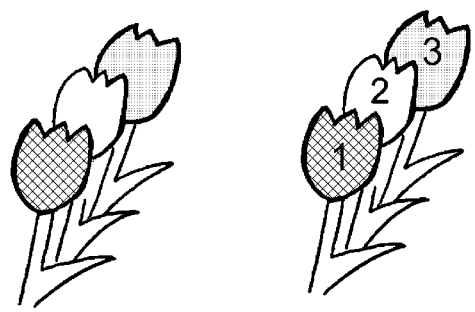
Figure 11:
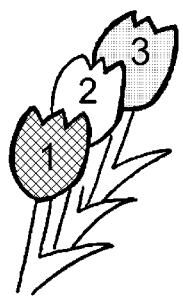

As shown in FIG. 11, at Working Example 5, a package was prepared at which displayed on the surface thereof were illustrations that were images of tulips, the frontmost flower being colored red, the flower behind and overlapped by that one being colored white, and the backmost flower further overlapped by that one being colored yellow, the infusion set of Working Example 4 being sterilized and sealed therewithin to produce an infusion set.

As Comparative Example 1, an infusion set in which, instead of the caps having lids and hydrophobic filters employed at Working Example 1, caps were employed that differed only with respect to the fact that they were not provided with lids for closing openings, but which in other respects was identical to Working Example 1, was manufactured.

As Comparative Example 2, an infusion set in which, instead of the three-way stopcocks employed at Working Example 1, three-way stopcocks were employed that did not have rotating mechanisms, but which in other respects was identical to Working Example 1, was manufactured.

As Comparative Example 3, an infusion set in which Y-tubing was employed instead of the three-way stopcocks having infusion tubing at secondary tubing branches that were employed at Working Example 1, and in which three-way stopcocks that did not have rotating mechanisms were employed instead of the three-way stopcocks having rotating mechanisms for emergency ports that were employed at Working Example 1, but which in other respects was identical to Working Example 1, was manufactured.

An infusion container having sealed therewithin physiological saline solution was suspended from an IV stand, the spike disposed at the upstream-most location in the infusion set was made to pierce the rubber seal of said infusion container, and priming and backpriming operations were initiated. Testing was respectively carried out using the respective infusion sets at Working Example 1 through Working Example 5 and at Comparative Examples 1 through 3.

As a result, regardless of which infusion set was used, it was observed that priming and backpriming of the infusion set could be completed as a result of only a single operation in which a spike was made to pierce the seal of an infusion container, the interior of the infusion set being filled with physiological saline solution, with only the air at the interior of the infusion set that was displaced by said physiological saline solution being exhausted by way of hydrophobic filters respectively provided at caps for installation on spikes and caps for installation on connectors for connection with intravenous drip needles. There was no leakage of physiological saline solution from any of the connections between/among the various members. At Working Example 2, because clips equipped with catches for flanges of spikes were provided on caps, the caps could be more securely installed on spikes than was the case elsewhere.

Next, following completion of priming and backpriming, the lids for closing the openings at the caps, at which hydrophobic filters were arranged and which were installed on the spikes at the foregoing respective infusion sets, were closed (Working Examples 1 through 5, Comparative Example 2, and Comparative Example 3). Note that there were no lids on the caps at Comparative Example 1. In addition, shutoff clamps 3 disposed at the respective sets of infusion tubing were pinched together, and roller clamp 10 was moved to its closed position, to close off the respective sets of infusion tubing. Furthermore, where three-way stopcocks were present, levers at three-way stopcocks were moved to positions corresponding to the intravenous drip infusion to be initiated.

Caps, at which hydrophobic filters were arranged and which were installed on the spikes at Working Examples 1 through 5 and Comparative Examples 1 through 3, were removed from spikes and connectors for connection with intravenous drip needles.

As a result, because the lids were closed at the caps at Working Examples 1 through 5, Comparative Example 2, and Comparative Example 3, air did not pass through the hydrophobic filters to reenter the cap interiors, and as a result of the action of surface tension due to the physiological saline solution and atmospheric pressure from the openings at the caps, physiological saline solution at regions peripheral to the hydrophobic filters at the interior did not spill out from the insertion ports at the caps. At Working Example 3, because caps were anchored to infusion tubing by C-shaped hooks, there was no concern that the caps would come off at the time that the spikes and the connectors for connection with intravenous drip needles were being detached. Furthermore, physiological saline solution did not drip out of the spikes or the connectors for connection with intravenous drip needles after they were detached.

However, at Comparative Example 1, which did not have lids, following removal of the caps from the spikes and the connectors for connection with intravenous drip needles, air did pass through the hydrophobic filters provided at those caps to reenter the cap interiors, and physiological saline solution that had remained at the cap interiors leaked out via the insertion ports for the spikes and connectors for connection with intravenous drip needles at the caps and spilled out to the exterior.

Next, following the foregoing operations, a new set of a plurality of infusion containers having sealed therewithin physiological saline solution were prepared, the spikes that had been removed from the respective foregoing infusion sets were made to pierce the rubber seals of the respectively different infusion containers, and those infusion containers were suspended from IV stands.

Because Working Examples 1 through 5 and Comparative Example 1 employed three-way stopcocks having rotatable mechanisms, it was possible by rotating the infusion tubing linked to the respective infusion containers to cause these to be suspended in well-balanced arrangements from the IV stands. Furthermore, while variation in the amount of physiological saline solution within the infusion containers did upset the balance of the IV stands, it was possible by rotating the infusion tubing linked to the respective infusion containers to again cause these to be suspended in well-balanced arrangements. Furthermore, it was possible to accomplish this without pulling on or otherwise applying unwanted force to the connector for connection with the intravenous drip needle provided at the downstream-most location in the infusion set.

However, because the infusion sets of Comparative Example 2 and Comparative Example 3 were such that the three-way stopcocks did not have rotating mechanisms, the orientations thereof could not be changed from the way in which they were configured at the time of manufacture, and so it was not an easy matter to cause these to be suspended in well-balanced arrangements from the IV stands. Furthermore, variation in the amount of physiological saline solution within the infusion containers further upset the balance of the IV stands. And when upon seeing this an attempt was made to alter the arrangement in a way that would adjust the balance, this on the contrary caused the infusion tubing to become twisted, in accompaniment to which it was observed that the connector for connection with the intravenous drip needle provided at the downstream-most location in the infusion set was subjected to pulling and other such unwanted forces.

At the infusion sets of Working Example 4 and Working Example 5, because some of the members making up the sets of secondary tubing were colored, it was possible with just a glance to recognize each set of secondary tubing and the spike at the far end thereof.

Furthermore, at the infusion set of Working Example 5, the illustrations depicted on the surface of the package immediately caught the eye, and it was possible to effortlessly recognize that red, white, and yellow coloring was employed in order from the frontmost depicted image to the images that were depicted therebehind. In addition, when the package was opened, it was possible with just a glance to recognize that some of the members making up the sets of secondary tubing in the infusion set that was sealed therewithin were colored with the same colors.

INDUSTRIAL UTILITY

In accordance with the means of the present invention, priming and backpriming operations can be carried out as a result of only a single operation in which a spike is made to pierce the seal of an infusion container containing physiological saline solution, and, there being no unintentional leakage of liquid while operations are being carried out or after operations have been carried out, it is possible to drastically reduce the risk of occurrence of damage to equipment and contamination of the hospital room interior, and the physiological saline solution can also be utilized in effective fashion during any medical treatment that may take place thereafter. Furthermore, it is possible to provide a novel infusion set that makes it possible to easily perform operations for alleviation of twisting and operations for adjustment of position of infusion tubing and/or infusion container(s) while maintaining the stability of the infusion set, and to prevent bodily pain to patients and/or leakage of liquid that might otherwise occur due to twisting and/or tension acting on the infusion set and/or intravenous drip needle(s) while lowering the risk of occurrence of accidents in which the IV stand from which the infusion set is suspended falls over. Moreover, it is possible to provide a novel infusion set that makes it possible to prevent occurrence of situations in which confusion as to order of use of a plurality of spikes provided at an infusion set when installing infusion container(s) causes error in the order in which infusions are to be administered, or in which infusion(s) containing different drug(s) become mixed up among multiple pieces of infusion tubing when there has been a change in set(s) of infusion(s) at the infusion set, and other accidents such as may occur due to human error, and that moreover makes it possible to easily establish standard procedures for use.

EXPLANATION OF REFERENCE NUMERALS

1 Cap for installation on spike
2 Spike

2a Flange
3 Shutoff clamp
4 Infusion tubing
4a Infusion tubing (sectional view)
5 Three-way stopcock
5a Primary tubing upstream branch connector
5b Primary tubing downstream branch connector equipped with mechanism that connects in such fashion as to permit rotation about primary tubing as axis
5c Secondary tubing branch connector
5d Lever
6 Cap for installation on spike (with hydrophobic filter and lid)
6a Insertion port for spike
6b Hydrophobic filter
6c Opening
6d Lid
6e Catch
6f Clip
6g C-shaped hook
6h O-shaped hook
6i U-shaped hook
7 Cap for installation on connector for connection with intravenous drip needle
7a Insertion port for connector for connection with intravenous drip needle
7b Hydrophobic filter
7c Opening
7d Lid
8 Male connector
9 Drip chamber
10 Roller clamp
11 Filter bag
12 Connector for connection with intravenous drip needle
13 Infusion container
14 Physiological saline solution
15 Package
16 Illustration

The invention claimed is:

1. An infusion set wherein it has a cap, for installation on a spike or a connector for connection with an intravenous drip needle, arranged at which there is an opening configured so as to not allow passage therethrough of solid or liquid but so as to allow passage therethrough of gas at the interior of the cap, a hydrophobic filter being arranged at a location inward from where the tip of the spike or the connector for connection with the intravenous drip needle is inserted at the interior of the cap by way of an insertion port for the spike or the connector for connection with the intravenous drip needle, and a lid at the exterior of said opening for closing said opening; the spike; a three-way stopcock having a primary tubing downstream branch connector equipped with a mechanism that connects in such fashion as to permit rotation about primary tubing as axis; a male connector; a drip chamber; a roller clamp; the connector for connection with the intravenous drip needle; infusion tubing; a shutoff clamp for pressing on and opening and/or closing a flow path within the infusion tubing; and an optional filter bag;

wherein a spike is provided at an upstream-most location in the infusion set, said spike being connected to one end of infusion tubing equipped with a shutoff clamp for pressing on and opening and/or closing a flow path within infusion tubing, the other end of said infusion tubing being connected to a primary tubing upstream branch connector of a three-way stopcock having a primary tubing downstream branch connector equipped with a mechanism that connects in such fashion as to permit rotation about primary tubing as axis, and connected to a secondary tubing branch connector at said three-way stopcock there is one end of infusion tubing equipped with a shutoff clamp for pressing on and opening and/or closing a flow path within infusion tubing, and a spike covered with the aforesaid cap at the other end of said infusion tubing, and further connected to a primary tubing downstream branch connector of said three-way stopcock there is or are optionally one or more three-way stopcocks connected to one end of infusion tubing equipped with shutoff clamps for pressing on and opening and/or closing flow paths within infusion tubing connected to spikes covered with caps for installation on the aforesaid spikes at secondary tubing branch connectors and having primary tubing downstream branch connectors equipped with mechanisms that connect in such fashion as to permit rotation about primary tubing as axes;

wherein a male connector is further connected to a primary tubing downstream branch connector of that which among the aforesaid three-way stopcocks is disposed at a downstream location, one end of infusion tubing equipped with a shutoff clamp for pressing on and opening and/or closing a flow path within infusion tubing being further connected thereto, and a drip chamber being connected to the other end of said infusion tubing, said drip chamber being connected to one end of infusion tubing on which a roller clamp is installed, the other end of said infusion tubing being connected to a primary tubing upstream branch connector of a three-way stopcock having a primary tubing downstream branch connector equipped with a mechanism that connects in such fashion as to permit rotation about primary tubing as axis, a primary tubing downstream branch connector of said three-way stopcock being connected to a male connector, one end of infusion tubing being further connected thereto, and optionally a filter bag and infusion tubing downstream therefrom being connected to the other end of said infusion tubing, and further connected to the other end of said infusion tubing there is a primary tubing upstream branch connector of a three-way stopcock having a primary tubing downstream branch connector equipped with a mechanism that connects in such fashion as to permit rotation about primary tubing as axis, a primary tubing downstream branch connector of said three-way stopcock being connected to a male connector, one end of infusion tubing being further connected thereto, and a connector for connection with an intravenous drip needle covered with a cap for installation on the aforesaid connector for connection with an intravenous drip needle being connected to the other end of said infusion tubing.

2. The infusion set according to claim 1, wherein the cap, for installation on the spike, arranged at which there is the opening not permitting passage therethrough of solid or liquid but permitting passage therethrough of gas, the hydrophobic filter being arranged at the location inward from where the tip of the spike is inserted at the interior of the cap by way of the insertion port for the spike, and the lid for closing said opening at the exterior of said opening, is provided with a clip equipped with a catch for a flange disposed on the spike.

3. The infusion set according to claim 2, wherein the cap, for installation on the spike, arranged at which there is the opening not permitting passage therethrough of solid or liquid but permitting passage therethrough of gas, the hydrophobic filter being arranged at the location inward from where the tip of the spike is inserted at the interior of the cap by way of the insertion port for the spike, and the lid for closing said opening at the exterior of said opening, has a hook for anchoring said cap to infusion tubing.

4. The infusion set according to claim 2, wherein a hook for anchoring the aforesaid cap to infusion tubing has a C-shaped configuration, an O-shaped configuration, or a U-shaped configuration.

5. The infusion set according to claim 2, wherein the aforesaid three-way stopcock at which infusion tubing is connected to a secondary tubing branch connector, said infusion tubing, a shutoff clamp linked thereto, a spike, and a cap for installation on a spike are grouped together as a single group such that one or more thereamong is colored with the same color; and where there are a plurality of three-way stopcocks at which spikes are connected to secondary tubing, groups belonging to adjacent three-way stopcocks are colored so as to be respectively different colors; and colored tape of the same color is optionally applied to said infusion tubing; and a number indicating order of administration is further optionally displayed at any among the three-way stopcock, infusion tubing, shutoff clamp, spike, cap for installation on the spike, and colored tape.

6. The infusion set according to claim 1, wherein the cap, for installation on the spike, arranged at which there is the opening not permitting passage therethrough of solid or liquid but permitting passage therethrough of gas, the hydrophobic filter being arranged at the location inward from where the tip of the spike is inserted at the interior of the cap by way of the insertion port for the spike, and the lid for closing said opening at the exterior of said opening, has a hook for anchoring said cap to infusion tubing.

7. The infusion set according to claim 6, wherein the cap, which covers the spike, which is for installation on the spike, and arranged at which there is the opening not permitting passage therethrough of solid or liquid but permitting passage therethrough of gas, the hydrophobic filter being arranged at the location inward from where the tip of the spike is inserted at the interior of the cap by way of the insertion port for the spike, and the lid for closing said opening at the exterior of said opening, is anchored by the aforesaid hook to infusion tubing connected to the spike disposed at the upstream-most location in the infusion set.

8. The infusion set according to claim 7, wherein the aforesaid three-way stopcock at which infusion tubing is connected to a secondary tubing branch connector, said infusion tubing, a shutoff clamp linked thereto, a spike, and a cap for installation on a spike are grouped together as a single group such that one or more thereamong is colored with the same color; and where there are a plurality of three-way stopcocks at which spikes are connected to secondary tubing, groups belonging to adjacent three-way stopcocks are colored so as to be respectively different colors; and colored tape of the same color is optionally applied to said infusion tubing; and a number indicating order of administration is further optionally displayed at any among the three-way stopcock, infusion tubing, shutoff clamp, spike, cap for installation on the spike, and colored tape.

9. The infusion set according to claim 6, wherein a hook for anchoring the aforesaid cap to infusion tubing has a C-shaped configuration, an O-shaped configuration, or a U-shaped configuration.

10. The infusion set according to claim 6, wherein the aforesaid three-way stopcock at which infusion tubing is connected to a secondary tubing branch connector, said infusion tubing, a shutoff clamp linked thereto, a spike, and a cap for installation on a spike are grouped together as a single group such that one or more thereamong is colored with the same color; and where there are a plurality of three-way stopcocks at which spikes are connected to secondary tubing, groups belonging to adjacent three-way stopcocks are colored so as to be respectively different colors; and colored tape of the same color is optionally applied to said infusion tubing; and a number indicating order of administration is further optionally displayed at any among the three-way stopcock, infusion tubing, shutoff clamp, spike, cap for installation on the spike, and colored tape.

11. The infusion set according to claim 1, wherein a hook for anchoring the aforesaid cap to infusion tubing has a C-shaped configuration, an O-shaped configuration, or a U-shaped configuration.

12. The infusion set according to claim 11, wherein the cap, which covers the spike, which is for installation on the spike, and arranged at which there is the opening not permitting passage therethrough of solid or liquid but permitting passage therethrough of gas, the hydrophobic filter being arranged at the location inward from where the tip of the spike is inserted at the interior of the cap by way of the insertion port for the spike, and the lid for closing said opening at the exterior of said opening, is anchored by the aforesaid hook to infusion tubing connected to the spike disposed at the upstream-most location in the infusion set.

13. The infusion set according to claim 11, wherein the aforesaid three-way stopcock at which infusion tubing is connected to a secondary tubing branch connector, said infusion tubing, a shutoff clamp linked thereto, a spike, and a cap for installation on a spike are grouped together as a single group such that one or more thereamong is colored with the same color; and where there are a plurality of three-way stopcocks at which spikes are connected to secondary tubing, groups belonging to adjacent three-way stopcocks are colored so as to be respectively different colors; and colored tape of the same color is optionally applied to said infusion tubing; and a number indicating order of administration is further optionally displayed at any among the three-way stopcock, infusion tubing, shutoff clamp, spike, cap for installation on the spike, and colored tape.

14. The infusion set according to claim 1, wherein the aforesaid three-way stopcock at which infusion tubing is connected to a secondary tubing branch connector, said infusion tubing, a shutoff clamp linked thereto, a spike, and a cap for installation on a spike are grouped together as a single group such that one or more thereamong is colored with the same color; and where there are a plurality of three-way stopcocks at which spikes are connected to secondary tubing, groups belonging to adjacent three-way stopcocks are colored so as to be respectively different colors; and colored tape of the same color is optionally applied to said infusion tubing; and a number indicating order of administration is further optionally displayed at any among the three-way stopcock, infusion tubing, shutoff clamp, spike, cap for installation on the spike, and colored tape.

15. The infusion set according to claim 14, wherein the aforesaid colored infusion set is further sealed within a package at which displayed in mutually offset and partially overlapping fashion on the surface thereof are a plurality of illustrations, the respective illustrations being respectively colored so as to have the same colors as the coloration given to groups within the infusion set sealed therewithin that comprise the aforesaid three-way stopcocks at which infusion tubing is connected to secondary tubing branch connectors, said infusion tubing, shutoff clamps linked thereto, spikes, and caps for installation on spikes.

16. The infusion set according to claim 15, wherein numbers indicating order of administration are further displayed at the aforesaid illustrations.

* * * * *